US010022430B2

(12) United States Patent
Grallert et al.

(10) Patent No.: US 10,022,430 B2
(45) **Date of Patent: *Jul. 17, 2018**

(54) CHIMERIC POLYPEPTIDES AND THEIR USE IN BACTERIAL DECOLONIZATION

(71) Applicant: HYPHARM GMBH, Bernried (DE)

(72) Inventors: Holger Grallert, Weilheim (DE); Sonja Molinaro, Weilheim (DE)

(73) Assignee: HYpharm GmbH (DE)

( * ) Notice: Subject to any disclaimer, the term of this patent is extended or adjusted under 35 U.S.C. 154(b) by 34 days.

This patent is subject to a terminal disclaimer.

(21) Appl. No.: 14/709,118

(22) Filed: May 11, 2015

(65) Prior Publication Data

US 2015/0238577 A1 Aug. 27, 2015

Related U.S. Application Data

(62) Division of application No. 13/513,095, filed as application No. PCT/EP2010/007941 on Dec. 23, 2010, now Pat. No. 9,057,059.

(30) Foreign Application Priority Data

Dec. 23, 2009 (EP) .................................... 09015998

(51) Int. Cl.

| | |
|---|---|
| ***A61K 38/48*** | (2006.01) |
| ***C12N 9/24*** | (2006.01) |
| ***C12N 9/52*** | (2006.01) |
| ***C07K 14/195*** | (2006.01) |
| ***C12N 9/50*** | (2006.01) |
| ***C12N 9/36*** | (2006.01) |

(52) U.S. Cl.

CPC ........ *A61K 38/4886* (2013.01); *C07K 14/195* (2013.01); *C12N 9/2462* (2013.01); *C12N 9/503* (2013.01); *C12N 9/52* (2013.01); *C07K 2319/33* (2013.01); *C12Y 304/24075* (2013.01)

(58) Field of Classification Search

None

See application file for complete search history.

(56) References Cited

U.S. PATENT DOCUMENTS

| | | | |
|---|---|---|---|
| 7,572,602 | B1 | 8/2009 | Donovan |
| 8,383,102 | B2 | 2/2013 | Donovan |
| 8,481,289 | B2 | 7/2013 | Donovan et al. |
| 2009/0130082 | A1 | 5/2009 | Kaplan |

FOREIGN PATENT DOCUMENTS

| | | |
|---|---|---|
| WO | 2007/130655 | 11/2007 |

OTHER PUBLICATIONS

Donovan, et al., "Peptidoglycan hydrolase fusions maintain their parental specificities," *Applied and Environmental Microbiology*, Apr. 2006, 72(4):2988-2996.

Becker, et al., "Differentially conserved staphylococcal SH3b_5 cell wall binding domains confer increased staphylolytic and streptolytic activity to a streptococcal prophage endolysin domain," *Gene*, Aug. 2009, 443(1-2):32-41.

Baba, et al., "Target Cell Specificity of a Bacteriocin Molecule: A C-Terminal Signal Directs Lysostaphin to the Cell Wall of *Staphylococcus aureus," EMBO Journal*, Jan. 1996, 15(18):4789-4797.

Becker, et al., "LysK CHAP endopeptidase domain is required for lysis of live staphylococcal cells," *FEMS Microbiology Letters*, May 2009, 294(1):52-60.

International Search Report for PCT/EP2010/007941, dated Mar. 15, 2011.

Horgan et al., "Phage Lysin LysK Can Be Truncated to Its CHAP Domain and Retain Lytic Activity against Live Antibiotic-Resistant Staphylococci", *Applied and Environmental Microbiology*, Feb. 2009, 75(3): 872-874.

Recsei et al., "Cloning, sequence, and expression of the lysostaphin gene from *Staphylococcus simulans", PNAS*, Mar. 1987, 84:1127-1131.

Donovan et al., "Peptidoglycan hydrolase enzyme fusions for treating multi-drug resistant pathogens," Biotech International, (21):6-10, Apr. 2009.

GenBank Entry: CAA29494.1 (Lysostaphin); Oct. 23, 2008.

GenBank Entry: AA047477.2 (LysK endolysin); May 6, 2004.

Heinrich et al., "The molecular organization of the lysostaphin gene and its sequences repeated in tandem," Mol Gen Genet, 209:563-569, 1987.

Oscariz et al., "Classification and mode of action of membrane-active bacteriocins produced by gram-positive bacteria," Int. Microbiol, 4:13-19, 2001.

*Primary Examiner* — Suzanne M Noakes

(74) *Attorney, Agent, or Firm* — Riverside Law LLP

(57) ABSTRACT

The present invention relates to chimeric polypeptides comprising a first portion, which comprises a bacteriocin cell wall-binding domain (CBD) and a second portion, which comprises an enzymatic active domain (EAD) selected from the lytic domain of a bacteriophage lysin, a bacteriocin and a bacterial autolysin. Provided are such chimeric polypeptides and variants and fragments thereof, nucleic acids encoding the same, vectors carrying such nucleic acids and host cells transformed or transfected with such vectors. The chimeric polypeptides of the present invention are useful for the reduction of certain bacterial populations, including methods and compositions for the treatment of various bacterial infections. For example, chimeric polypeptides of the present invention have been shown to effectively kill various bacteria, including methicillin-resistant *Staphylococcus aureus* (MRSA), as well as other human pathogens. Thus, provided are compositions comprising chimeric polypeptides according to the present invention, variants or fragments thereof, and the use of such compositions in prophylaxis or therapy of bacterial diseases, bacterial infections or bacterial colonizations.

18 Claims, 3 Drawing Sheets

Figure 2
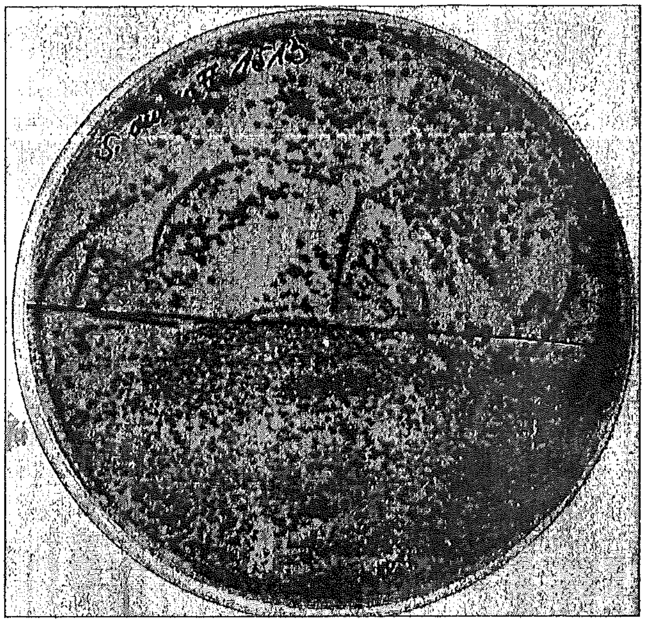
Figure 2A
Control: Upper half of the plate was treated with gel containing no protein
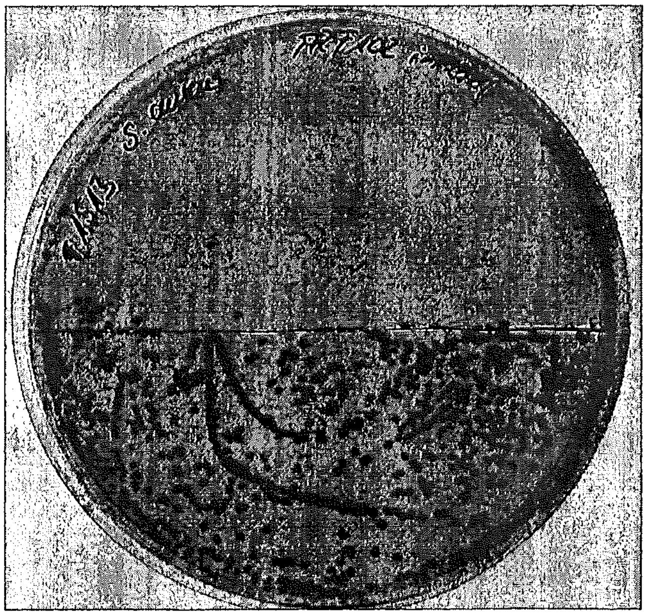
Figure 2B
Upper half was treated with gel containing 10 μg PRF102

CHIMERIC POLYPEPTIDES AND THEIR USE IN BACTERIAL DECOLONIZATION

CROSS-REFERENCE TO RELATED APPLICATION

The present application is a divisional of U.S. patent application Ser. No. 13/519,095, filed on Sep. 17, 2012, which is a 35 U.S.C. § 371 national phase application from, and claiming priority to, International Application No. PCT/EP2010/007941, filed Dec. 23, 2010, and published under PCT Article 21(2) in English, which claims priority to European Application No. EP 09015998.9, filed Dec. 23, 2009, all of which applications are incorporated by reference herein in their entireties.

TECHNICAL FIELD

The present invention relates to chimeric polypeptides comprising a bacteriocin cell binding domain (CBD) and at least one enzymatic active domain (EAD) having bacterial cell wall lytic activity, which are useful in therapy and prophylaxis of pathogenic bacterial colonisation, including bacterial infections and bacterial diseases.

BACKGROUND OF THE INVENTION

The rapidly increasing number of antibiotic resistant bacteria is a growing challenge for medicine and health care systems worldwide. Especially, the number of infections with methicillin-resistant *Staphylococcus aureus* (MRSA) increases dramatically in developed countries. In the Netherlands, hospital acquired infections are managed successfully by screening of patients entering hospital for MRSA carrier and consequent decolonisation of such patients. The established strategy of decolonisation of *S. aureus* from patients is eradication of *S. aureus* in nose using an antibiotic (for example, mupirocin) and decolonisation of skin using disinfectants. Problems of this decolonisation regimen are (i) extensive use of antibiotics, (ii) upcoming resistance of *S. aureus* against antibiotics (for example, against mupirocin), (iii) high costs due to very long treatment time (normally 5-7 days), and (iv) opportunistic infections due to complete eradication of natural skin flora.

Considering these severe disadvantages, the community is seeking for alternative approaches for effective decolonisation within short time and avoiding the use of antibiotics. Lysins, which are bacteriophage-induced lytic or hydrolytic enzymes responsible for bacterial host lysis, offer such advantages in general but they have to be optimized for various aspects. Bacteriophage (phage) lysins have been designated using various names including lysins, phage-lysins, virolysins, and endolysins. Structurally, lysins are commonly found as modular proteins with at least one domain that confers the enzymatic activity for hydrolysing specific bonds in the murein or peptidoglycan layer of the bacterial cell wall (enzymatic active domain—EAD), and one domain that confers binding specificity to a carbohydrate epitope of the cell wall (cell binding domain—CBD). Thus, lysin family members (cell wall or peptidoglycan hydrolases) exhibit a modular design in which a catalytic domain is fused to a specificity or binding domain.

During the bacteriophage (phage) reproduction cycle, after assembly of the new phage particles, lysins (endolysins) are produced to destroy the bacterial cell wall. Endolysins can be divided in into five classes according to their cell wall lytic activities: (1) N-Acetylmuraminidases (lysozymes), (2) Endo-β-N-acetylglucosaminidases, (3) Lytic transglycosidases, (4) N-acetylmuramoyl-L-alanine amidases, and (5) Endopeptidases. While the aforementioned (1) to (3) all cleave within the sugar moiety of the peptidoglycan, (4) cleaves at the amid bond between the sugar backbone and the peptide linker and (5) cleaves within the peptide cross bridge.

Endolysins are described as having a narrow spectrum regarding their target. In case of Gram-positive bacteria, endolysins act on cell walls from inside as well as from outside, thus, making these molecules to antimicrobial drug candidates (Borysowski et al. 2006). While bacteriophage host ranges are largely restrictive, i.e. recognizing only one specific antigen on its bacterial host, phage lysins are less restrictive, recognizing a specific carbohydrate molecule common to the particular species of host bacteria. Although the range of bacteria targeted by lysins is less restrictive than the corresponding bacteriophage, lysins still maintain a degree of specificity, having minimal effects on other bacteria including commensal organisms.

The use of endolysins to kill bacteria was disclosed for the first time by Gasson in 1991 (GB 2 255 561). Further therapeutic and prophylactic applications, including animal model systems, have been described by Nelson et al. 2001. This work describes a topical application of endolysins against group A streptococci and pneumococci in oral and nasopharyngeal treatment. In the field of staphylococcal treatment with bacteriophage derived lysins, Rashel et al. 2007 have shown that endolysin from phage phiMR11 is able to eradicate MRSA in nares of mice and protects mice by intraperitoneal injection from septic death. Further regimes of treatment and pharmaceutical compositions to treat and prevent bacterial infections using phage derived lysins are described in U.S. Pat. No. 5,997,862. However, in all so far published examples using bacteriophage derived endolysins for the treatment of bacterial infections, the amount of protein for an effective treatment is very high. This is due the poor stability of the enzymes and due to inhibition of the activity in application relevant matrices.

In case of lysins against *Staphylococcus* bacteria, a number of wild-type endolysins have been cloned and characterized. For example, protein 17 from phage P68 is a staphylococcal endolysin, which is reported to exhibits antimicrobial activity against *S. aureus* isolates including clinical isolates (Takác and Bläsi 2005). Various groups investigated the endolysin of *S. aureus* bacteriophage phi11 in antimicrobial applications. Navarre et al. 1999 identified two enzymatic activities domains (amidase and endopeptidase) in phi11 lysin and showed that a mutant with deletion of the amidase domain is still active. Mutants of phi11 (and phi12) endolysin have been characterized by different activity assays on *S. aureus* cell walls, heat inactivated bacteria and on bacterial biofilms (Sass and Bierbaum 2007). All these investigations have in common that they are using artificial experimental conditions for functional characterization of the endolysins. Therefore, no evidences regarding efficacy on living cells under application-relevant conditions can be drawn from these publications.

Another staphylolytic enzyme is derived from bacteriophage phiK. This endolysin, called lysK, has been characterized in more detail by the groups of David M. Donavan and R. Paul Ross (O'Flaherty et al. 2005; WO 2008/001342; Becker et al. 2008; Horgan et al. 2009). They have been able to show, that lysK has a broad bactericidal activity against living *staphylococcus* bacteria without discriminating between the different genera. LysK consists of one CBD and two EADs, a cysteine-histidine amino peptidase (CHAP)

and an amidase domain. Expressing the individual EAD's, they were able to show that the CHAP domain alone is sufficient for killing but not the amidase domain. A deletion mutant, without amidase domain (lysKΔ221-390), possesses the same killing activity as the wild type protein. Determining MIC values for the truncation/deletion constructs, only MIC values for the wild type LysK and the lysKΔ221-390 were measurable in TSB medium. The CHAP domain alone showed no measurable activity within such a complex matrix. The determined MIC values are considerably high, 78 μg/ml and 63 μg/ml for wild type lysK and lysKΔ221-390, respectively. No chimeric lysin based on lysK domains has been described so far.

All published data using wild type endolysins clearly show that these molecules are quite effective in killing bacteria in buffer solutions. The advantage of these molecules is the very fast onset time (minutes to hours), and the mode of action from outside without involvement of metabolic processes within the cell. As a matter of fact, for endolysins induction/acquisition of resistance has not been described in literature. On the other hand, wild type endolysins tend to be quite unstable at elevated temperatures and functionality is reduced in complex compositions like culture media or biological fluids. All published MIC values (minimal inhibitory concentration) or MBC values (minimal bactericidal concentration) are in the range >50 μg/ml. It can be speculated that in many cases MIC values are not reported for experimental reasons.

Enzymes with cell wall degrading properties similar to bacteriophage lysins (endolysins) can also be found in bacteria. Autolysins are bacteriolytic enzymes that digest the cell-wall peptidoglycan of the bacteria that produce them. Autolysins are involved in cell wall reconstruction during bacterial cell division. Although potentially lethal, autolysins appear to be universal among bacteria that possess peptidoglycan. "Autolysin" is the term used for lysins, which are produced by bacteria and involved in cell division, while the term "lysin" or "endolysin" refers to lytic enzymes, which are involved in phage release, as described herein above. Bacteriocins are molecules also produced and secreted by microorganisms. They are antibacterial substances of a proteinaceous nature that are produced by different bacterial species. A subclass of bacteriocins consists of enzymes (proteinaceous toxins) which are produced by bacteria to inhibit the growth of similar or closely related concurrence bacterial strain(s) in their habitat. Many bacteria produce antimicrobial bacteriocin peptides. They also contain CBDs and EADs. Bacteriocins target prokaryotes but not eukaryotes, making them safe for human consumption.

The bacteriocin lysostaphin is naturally produced by *Staphylococcus simulans* to combat *Staphylococcus aureus*. It is highly effective in vitro and capable of killing bacteria in complex media (Kumar J. 2008). Lysostaphin consists of one CBD and one glycyl-glycine endopeptidase domain, which cleaves the characteristic penta-glycine cross bridge in *S. aureus* cell walls. This molecule has been tested in various animal models and exhibit good efficacy even in complex matrices (Kokai-Kun et al. 2007; Kusuma et al. 2007). The reported MIC values of lysostaphin are more than 1000-fold lower compared to lysK (<0.02 μg/ml). The major disadvantage of lysostaphin is the occurrence of resistance in *S. aureus*. Two different genetic escape mechanisms have been described so far: First, incorporation of serine into the penta-glycine bridge (DeHart et al. 1995). Secondly, shortening of the glycine bridge; gly3 or gly2 (Ehlert et al. 1997; Strandén et al. 1997). It can be assumed that such monogenic resistance marker will rapidly be selected under selection pressure.

Enzymatic active domains (EADs) can further be found in structural bacteriophage proteins. They are part of the early infection machinery of the bacteriophage, locally hydrolyzing the cell wall prior to DNA injection.

In order to deal with the fact of resistance development, groups started to investigate the combination of different lysins. For example, synergistic effects between lysK and lysostaphin (Becker et al. 2008) have been described, resulting in reduced effective concentrations for killing *S. aureus*. The drawback of this concept is, that in case of occurrence of resistance against one component (for example, lysostaphin), the concentration of the second component will not be effective anymore. Furthermore, a composition with two active components is difficult to develop and expensive in production.

It is known that a combination of domains (CBD's and EAD's) from different source organisms is possible. However, the purpose of such domain exchange experiments was always to alter or broaden the host specificity of the lysins (Diaz et al. 1990; Croux et al. 1993; Donovan et al. 2006). So far, no systematic domain exchange experiments have been performed with endolysin-derived EAD's to obtain lytic molecules with improved properties with respect to efficacy, resistance potential and stability.

There is one example in the literature to construct a highly stable chimeric lysin based on a lysostaphin CBD fused to a tail associated murein-degrading enzyme (TAME) domain (WO 2007/130655). This domain can be considered as stable as it is a part of a bacteriophage structural protein. The disadvantage of such constructs is the very low specific activity compared to endolysins. Therefore, more protein is required to reach effective concentrations. Furthermore, inhibition of the molecules in complex matrices cannot be excluded because no characterization in this regard has been provided.

There is an ongoing need for therapies and agents effective in the control of bacterial contamination, colonization and infection. A major problem in medicine has been the development of drug resistant bacteria as more antibiotics are used for a wide variety of illnesses and other conditions. The over utilization of antibiotics has increased the number of bacteria showing resistance. Furthermore, broadly reactive antibiotics can affect normal flora and can cause antibiotic resistance in these organisms because of the frequency of drug use. The number of people becoming hyper allogenic to antibiotics appears to be increasing because of antibiotic overutilization. Accordingly, there is a commercial need for new antibiotics (or bacterial killing substances), especially those that operate in new modalities or provide new means to kill pathogenic bacteria.

SUMMARY OF THE INVENTION

The use of lytic domains of a bacteriophage endolysin, a bacteriocin or a bacterial autolysin, specifically lytic domains of bacteriophage derived endolysins, for the treatment of bacterial infections is a promising alternative to overcome the increasing number of antibiotic resistance in bacteria. As shown in principle by a number of investigators, it is possible to kill bacteria in vitro and in animal models. Advantage of such lytic proteins is the fast onset of action and the lower risk of resistance development against these enzymes. As a general drawback, all the studies so far have shown that relatively high concentration of lysine is required for complete eradication of the target bacteria. The reason for the need of such high concentrations can be explained with reduced activity of the molecules in complex matrices and their low stability at elevated temperature. Application relevant activity data like (i) MIC values in bacterial growth media, (ii) MBC values in application relevant matrices (serum, growth media, mucin etc.), (iii) Log values of cfu reduction in relevant matrices (serum, growth media, mucin etc.), (iv) lysin activity in dependence of bacterial growth phase, and (v) pH range of activity, have therefore been rarely published. A further disadvantage of current staphylococcal lysins is that they tend to be rather unstable and often show poor solubility.

The present invention successfully provides new chimeric polypeptides against Gram-positive bacteria, *Staphylococcus aureus*, specifically including MRSA, with substantially improved efficacy in relevant matrices like culture media, mucin or serum. In addition, the chimeric polypeptides according to the present invention exhibit excellent thermal stability and good solubility. The activity of the chimeric polypeptides according to the present invention may not be dependent on the bacterial growth phase. The chimeric polypeptides provided by the present invention are useful in the treatment and prophylaxis of pathogenic bacterial colonisation, including bacterial infections and bacterial diseases, specifically pathogenic Gram-positive bacteria including pathogenic *Staphylococcus* bacteria.

The present invention provides the following items:

[1] A chimeric polypeptide comprising a first portion and a second portion joined by a linker, wherein (a) said first portion comprises an amino acid sequence of a bacteriocin cell binding domain (CBD); and (b) said second portion comprises an amino acid sequence of at least one enzymatic active domain (EAD) selected from (i) the lytic domain of a bacteriophage lysin;

(ii) the lytic domain of a bacteriocin; and (iii) the lytic domain of a bacterial autolysin.

[2] The chimeric polypeptide of item [1], wherein the lytic domain of (i) has at least 80%, preferably 90%, amino acid sequence identity with the polypeptide of SEQ ID NO: 1.

[3] The chimeric polypeptide of item [1], wherein the lytic domain of (ii) has at least 80%, preferably 90%, amino acid sequence identity with the polypeptide of SEQ ID NO: 2.

[4] The chimeric polypeptide of item [1], wherein the lytic domain of (iii) has at least 80%, preferably 90%, amino acid sequence identity with the polypeptide of SEQ ID NO: 3.

[5] The chimeric polypeptide of any one of items [1] to [4], wherein the CBD has at least 80%, preferably 90%, amino acid sequence identity with the polypeptide of SEQ ID NO: 4.

[6] The chimeric polypeptide of any one of items 1 to 5, having at least 80%, preferably 90%, amino acid sequence identity with the polypeptide of SEQ ID NO: 9, SEQ ID NO: 10, SEQ ID NO: 11, or SEQ ID NO: 15, and having essentially the same biological activity as the corresponding polypeptide of SEQ NO: 9, SEQ ID NO: 10, SEQ ID NO: 11, or SEQ ID NO: 15.

[7] The chimeric polypeptide of any one of items [1] to [6], having a MIC value ≤10 μg/ml, preferably ≤1 μg/ml, and more preferably ≤0.1 μg/ml.

[8] The chimeric polypeptide of any one of items [1] to [6], having an MBC (99.99%) value of ≤0.5 μg/ml, preferably ≤0.05 μg/ml.

[9] The chimeric polypeptide of any one of items [1] to [6], having a thermal stability (Tm) ≥45° C., preferably ≥50° C.

[10] The chimeric polypeptide of any one of items [1], [2], [5] and [6], wherein the bacteriophage lysin is a bacteriophage endolysin.

[11] The chimeric polypeptide of item [10], wherein the bacteriophage endolysin is lysK.

[12] The chimeric polypeptide of item [11], wherein the lytic domain is the lytic CHAP domain of lysK.

[13] The chimeric polypeptide of any one of items [1], [3], [5] and [6], wherein the bacteriocin lytic domain is the lytic domain of lysostaphin.

[14] The chimeric polypeptide of any one of items [1] and [4] to [6], wherein the bacterial autolysin is lytN.

[15] The chimeric polypeptide of any one of items [1] to [14], wherein the lytic domain exhibits the activity of an amidase, an endopeptidase, or a glycosidase.

[16] The chimeric polypeptide of item [15], wherein the glycosidase is a muramidase, a glucosaminidase, or a transglycosylase.

[17] The chimeric polypeptide of item [15], wherein the amidase is a N-acetylmuramyl-L-alanine amidase.

[18] The chimeric polypeptide of item [15], wherein the peptidase is a D-alanyl-glycyl-endopeptidase or a glycylglycyl-endopeptidase.

[19] The chimeric polypeptide of any one of items [1] to [18], wherein the CBD is a lysostaphin CBD.

[20] The chimeric polypeptide of any one of items [1] to [19], wherein the linker comprises at least one peptide bond.

[21] A nucleic acid molecule encoding the chimeric polypeptide of any one of items [1] to [20].

[22] A composition comprising the chimeric polypeptide of any one of items [1] to [20].

[23] A formulation, preferably a topical formulation, comprising the chimeric polypeptide of any one of items [1] to [20].

[24] The formulation of item [23], which is in the form of a bioadhesive, a medicated plaster, or a skin patch.

[25] The chimeric polypeptide of any one of items [1] to [20], the composition of item [22], or the formulation of item [23] or [24], for use in prophylaxis or therapy.

[26] The chimeric polypeptide of any one of items [1] to [20], or the composition of item [22], for use in treating or preventing a bacterial disease, a bacterial infection or bacterial colonization.

[27] Use of the chimeric polypeptide of any one of items [1] to [20], or the composition of item [22], for the preparation of a medicament for treating or preventing a bacterial disease, a bacterial infection or bacterial colonization.

[28] The chimeric polypeptide or composition of item [26], or the use of item [27], wherein the lytic activity (a) decreases the occurrence or severity of a local or systemic bacterial disease or bacterial infection, or (b) prevents or eliminates bacterial colonization.

[29] The chimeric polypeptide, composition or use of item [28], wherein the bacterial disease, bacterial infection or bacterial colonization are caused by Gram-positive bacteria.

[30] The chimeric polypeptide, composition or use of item [29], wherein the Gram-positive bacteria is *Staphylococcus*, preferably *Staphylococcus aureus*, and more preferably methicillin-resistant *Staphylococcus aureus* (MRSA).

[31] The chimeric polypeptide or composition of any one of items [26] and [28] to [30], or the use of any one of items [26] to [30], wherein the bacterial disease, bacterial infection or bacterial colonization is a bacterial disease, a bacterial infection or bacterial colonization of the skin or a mucous membrane, preferably the mucous membrane of the upper respiratory tract, more preferably the mucous membrane of the nasal cavity.

[32] The chimeric polypeptide, composition or use of item [31], further comprising a pharmaceutically acceptable carrier.

[33] The chimeric polypeptide, composition or use of item [32], wherein the carrier is aqueous, preferably selected from the group consisting of a cream, a gel, a lotion, and a paste.

The chimeric polypeptides of the present invention are targeted against specific pathogenic bacteria and these do not interfere with the normal bacterial flora. Also, chimeric polypeptides of the present invention primarily attack cell wall structures, which are not affected by plasmid variation. The actions of the enzymatic active domains of the chimeric polypeptides of the present invention are fast and may not depend on bacterial growth. The chimeric polypeptides of the present invention can be directed to the mucosal lining, where, in residence, they can kill colonizing bacteria, specifically Gram-positive bacteria, more specifically *Staphylococcus* strains, still more specifically species and subspecies of *Staphylococcus aureus*, and most specifically MRSA.

BRIEF DESCRIPTION OF THE DRAWINGS

FIG. 2 shows the results of treatment of *Staphylococcus aureus* on LB-Agar plates with a chimeric polypeptide of the present invention (Example 10). FIG. 2A represents the control experiment.

DETAILED DESCRIPTION OF THE INVENTION

Figure 1:
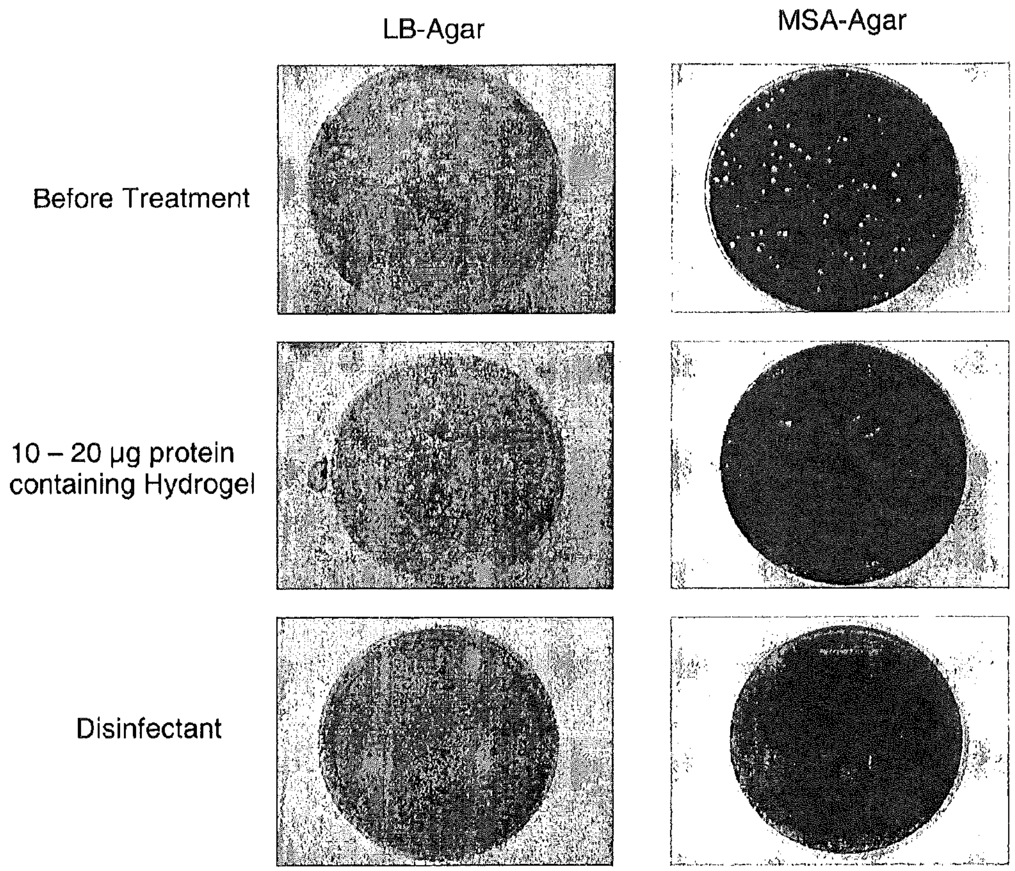
FIG. 1 shows the results of treatment of a human skin with a chimeric polypeptide of the present invention (Example 9). "Disinfectant" represents the positive control. "Before treatment" represents the negative control.

Chimeric polypeptides provided by the present invention have killing activity against two or more bacterial strains, preferably Gram-positive bacterial strains. In one aspect, the chimeric polypeptides exhibit a lytic effect on multiple bacterial strains, including multiple Gram-positive strains, preferably *Staphylococcus* strains, more preferably *Staphylococcus aureus* strains. Specifically, the present invention provides chimeric polypeptides for the treatment and prevention of *Staphylococcus aureus* infections.

The foregoing has outlined the features of various embodiments in order that the detailed description that follows may be better understood. Additional features and advantages of various embodiments will be described hereinafter which form the subject of the claims of the invention.

In one aspect, the chimeric polypeptides of the present invention are useful for application, in particular topical application, for decolonisation of Gram-positive bacteria, specifically *Staphylococcus aureus* and methicillin-resistant *S. aureus* (MRSA), based on the enzymatic activity of the lytic domain(s) in combination with improved activity, stability and specificity of the chimeric polypeptides. It was surprisingly found that a chimeric polypeptide according to the present invention shows improved lytic activity, improved host selectivity and stability compared to wild type endolysins. Specifically, an improved activity (expressed by MIC value) and improved stability was found for a chimeric polypeptide, which comprises a first portion and a second portion, wherein said first portion comprises an amino acid sequence of the CBD of lysostaphin, preferably the CBD of SEQ ID NO: 4, and wherein said second portion comprises an amino acid sequence of the CHAP domain of lysK, preferably the CHAP domain of SEQ ID NO: 1. Such a chimeric polypeptide has also proven to exhibit an improved host selectivity, preferably for *Staphylococcus* strains.

Likewise, an improved activity (expressed by MIC value) and improved stability was found for a chimeric polypeptide, which comprises a first portion and a second portion, wherein said first portion comprises an amino acid sequence of the CBD of lysostaphin, preferably the CBD of SEQ ID NO: 4, and wherein said second portion comprises an amino acid sequence of the CHAP domain of lysK, preferably the CHAP domain of SEQ ID NO: 1, and an amino acid sequence of the lytic domain of lysostaphin, preferably the lytic domain of SEQ ID NO: 2. Such a chimeric polypeptide has also proven to exhibit an improved host selectivity, preferably for *Staphylococcus* strains.

In another aspect, the chimeric polypeptides of the present invention posses MIC values lower than 10 μg/ml, preferably lower than 1 μg/ml, still more preferably lower than 0.3 μg/ml, and most preferably lower than 0.1 μg/ml.

In a still further aspect, the chimeric polypeptides of the present invention posses MBC (99.99%) values for 4 log reduction of living bacterial cells lower than 10 μg/ml, preferably lower than 1 μg/ml, more preferably lower than 0.5 μg/ml, still more preferably lower than 0.05 μg/ml, and most preferably lower than 0.01 μg/ml. It is an object of the present invention that the MBC values for 4 log reduction of bacterial cells of the chimeric polypeptides provided herein is not significantly inhibited in complex matrices like mucin and/or blood and/or serum.

In one embodiment of the present invention, at least one enzymatic active domain (EAD) is used, which cleaves between highly conserved residues within the peptide cross bridge of *S. aureus* cell walls.

In one aspect, the present invention provides chimeric polypeptides, which are optimized as they allow discriminating between *S. aureus* and other staphylococcal species.

In a further aspect, the chimeric polypeptides of the present invention are highly active and posses improved stability.

In the present invention, the term "CBD" represents the abbreviation for cell binding domain, more specifically cell wall binding domain. Thus, the term "CBD" may also represent the abbreviation for cell wall binding domain. The terms "cell binding domain" and "cell wall binding domain" may be used interchangeably. The structural and functional definition of a CBD according to the present invention is given elsewhere in the description.

In the present invention, "EAD" represents the abbreviation for enzymatic active domain. The structural and functional definition of an EAD according to the present invention is given elsewhere in the description.

A "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the domains stem from a different source or different origin. Specifically, a "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the domains stem from a different source organism, or source enzyme. In other words, the domains stem from a different origin of organism or different origin of enzyme. In this context, the terms "protein" and "peptide" may be used interchangeably with the term "enzyme". In other words, a "chimeric polypeptide" of the present invention is a polypeptide, which comprises heterologous domains.

In the present invention, the chimeric polypeptide comprises a first and a second portion, wherein the first portion generally comprises an amino acid sequence of a bacteriocin CBD. Bacteriocins are molecules produced by microorganisms. Thus, if the second portion of the chimeric polypeptide comprises an amino acid sequence of the lytic domain of a bacteriophage lysin as the EAD, the chimeric polypeptide is chimeric due to the fact that the CBD stems from a microorganism while the EAD stems from a bacteriophage.

In one aspect of the present invention, a "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the EAD is the lytic domain of a bacteriophage lysin. Preferably, the EAD is the lytic domain of a bacteriophage endolysin. More preferably, the EAD is the lytic domain of a bacteriophage endolysin, wherein the bacteriophage is from a Gram-positive bacterium. Still more preferably, the EAD is the lytic domain of a bacteriophage endolysin, wherein the bacteriophage is from a species or sub-species of *Staphylococcus*. In a more preferred embodiment, the EAD is the lytic domain of lysK, specifically the CHAP domain of lysK. Most preferably, the EAD comprises the amino acid sequence of SEQ ID NO: 1.

In another aspect, a "chimeric polypeptide" according to the present invention is a combination of a first portion and a second portion, wherein the first portion and the second each comprise an amino acid sequence of domains, CBD and EAD(s), wherein the CBD and EAD(s) are from different bacteriophages. More preferably, the domains are from different bacteriophages infecting Gram-positive bacteria.

In one aspect of the present invention, a "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the EAD is the lytic domain of a bacteriocin. Preferably, the EAD is the lytic domain of bacteriocin from a Gram-positive bacterium. More preferably, the EAD is the lytic domain of a bacteriocin from a species or sub-species of *Staphylococcus*, specifically from *S. simulans*. Still more preferably, the EAD is the lytic domain of lysostaphin. Most preferably, the EAD comprises the amino acid sequence of SEQ ID NO: 2.

In one aspect of the present invention, a "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the EAD is the lytic domain of a bacterial autolysin. If the EAD is the lytic domain of a bacterial autolysin, the chimeric polypeptide is chimeric due to the fact that the CBD stems from a bacteriocin while the EAD stems from a bacterial autolysin. The person skilled in the art is fully aware of proteins, which are classified as being bacteriocins and those, which are classified as being bacterial autolysins. In a preferred embodiment, a "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the EAD is the lytic domain of an autolysin from a Gram-positive bacterium. More preferably, the EAD is the lytic domain of an autolysin from a species or sub-species of *Staphylococcus*. Still more preferably, the EAD is the lytic domain of lytN or lytM, specifically the CHAP domain of lytN or lytM. Most preferably, the EAD comprises the amino acid sequence of SEQ ID NO: 3.

As defined herein, the first portion of the chimeric polypeptide of the present invention is defined to comprise an amino acid sequence of a bacteriocin cell wall-binding domain (CBD). Furthermore, as defined herein, the second portion of the chimeric polypeptide of the present invention is defined to comprise an amino acid sequence of at least one enzymatic active domain (EAD) selected from the lytic domain of a bacteriophage lysin, the lytic domain of a bacteriocin, and the lytic domain of a bacterial autolysin. Thus, by way of definition, one may consider that the chimeric polypeptide of the present invention may comprise the cell binding domain of a bacteriocin and the lytic domain of a bacteriocin. Lysostaphin is a bacteriocin, which comprises a cell binding domain and a lytic domain in form of an endopeptidase. However, lysostaphin is excluded from the definition of a chimeric polypeptide of the present invention since by way of definition a chimeric polypeptide of the present invention comprises a first portion and a second portion, wherein the first portion comprises an amino acid sequence of a bacteriocin cell binding domain (CBD) and the second portion comprises at least one enzymatic active domain (EAD), wherein the domains stem from a different source organism or source enzyme. Thus, in the present invention, it is excluded that the CBD and the EAD both stem from the bacteriocin lysostaphin, specifically from the lysostaphin naturally produced by *Staphylococcus simulans*. At least by way of defining the polypeptides of the present as being "chimeric", i.e. comprising "heterologous" domains as explained herein above, lysostaphin is excluded from this definition since lysostaphin is not composed of heterologous domains.

In the present invention, the source or origin of the domains comprised by the first and second portion of the chimeric polypeptide of the present invention is different. This does not mean that while the first portion comprises by way of definition a bacteriocin CBD, the second portion may not comprise at least one enzymatic active domain (EAD), which is a lytic domain of a bacteriocin, although lysostaphin is excluded as a chimeric polypeptide of the present invention. That is, the CBD and the EAD of the chimeric polypeptide of the present invention may not find their origin in the same bacteriocin, but may find their origin in different bacteriocins. Bacteriocins are different from each other when they stem from a different source or origin of organism. Bacteriocins are also different from each other when they do not recognize members of the same, but of closely related or different species by binding receptor sites on sensitive, or susceptible, organisms. Furthermore, a chimeric polypeptide of the present invention may comprise a CBD and an EAD from the same source or origin of organism, provided that the chimeric polypeptide comprises at least one further EAD from a different source or origin of organism or from a different source or origin of enzyme.

A chimeric polypeptide according to the present invention may comprise more than one enzymatic active domain and, thus, can act on different molecules, and hence has the potential to treat two or more different bacterial infections at the same time. Likewise, a chimeric polypeptide according to the present invention may also be used to treat a bacterial infection by cleaving the cell wall in more than one location.

In one embodiment, a "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the domains are from different pathogenic bacterial species or different pathogenic bacterial sub-species, preferably from different pathogenic Gram-positive bacterial species or different pathogenic Gram-positive bacterial sub-species, and more preferably from different pathogenic *Staphylococcus* species or different pathogenic *Staphylococcus* sub-species.

A pathogenic bacterial species or sub-species is defined by the similarities found among its members. Properties such as biochemical reactions, chemical composition, cellular structures, genetic characteristics, and immunological features are used in defining a pathogenic bacterial species or sub-species and thus differentiating different pathogenic bacterial species and sub-species.

In another embodiment, a "chimeric polypeptide" according to the present invention is a combination of a first portion and a second portion, wherein the first portion comprises an amino acid sequence of a bacteriocin cell binding domain (CBD) and the second portion comprises at least one enzymatic active domain (EAD), wherein the at least one EAD stems from a bacteriophage.

The chimeric polypeptide of the present invention comprises a first portion and a second portion joined by a linker, wherein said first portion comprises an amino acid sequence of a bacteriocin cell binding domain (CBD). In a preferred embodiment, the bacteriocin CBD of the present invention is a CBD produced by a Gram-positive bacterium. More preferably, the bacteriocin CBD of the present invention is a *Staphylococcus* bacteriocin CBD. In a more preferred embodiment of the present invention, the bacteriocin CBD is the CBD of lysostaphin. The bacteriocin lysostaphin is naturally produced by *Staphylococcus simulans*. Most preferably, in the present invention the bacteriocin CBD comprises the amino acid sequence of SEQ ID NO: 4.

A bacteriocin CBD according to the present invention is supposed to encompass herein all those bacteriocin protein domains, which are part of bacteriocin proteins binding to a target bacterium, specifically to the cell wall of a target bacterium. The cell binding domain or cell wall binding domain according to the present invention is that part of a bacteriocin cell binding protein or bacteriocin cell wall binding protein, which is necessary and sufficient for the bacterial cell binding ability, specifically the cell wall binding ability.

As described above, bacteriocin CBDs of the present invention are defined as being derived from proteins or enzymes of bacteriocin origin, which are capable of specific binding to bacteria. In this context, "derived from" refers to those CBDs, which maintain their binding ability, but have no or no significant hydrolytic activity. No or no significant hydrolytic activity in this context is intended to describe the situation whereby the hydrolytic activity is not sufficient to prevent the application of a bacteriocin CBD to bind to a cell, more specifically to a cell wall. A bacteriocin CBD according to the present invention is supposed to be a protein, which does not have any hydrolytic activity itself. This also applies to fragments and variants of a bacteriocin CBD according to the present invention, which are described herein and which are also encompassed by the present invention.

A bacteriocin CBD according to the present invention binds to bacterial cells, specifically to cell walls of target bacteria, more specifically to cell wall components coded by the target cell DNA, and still more specifically to cell wall components coded by the target cell DNA, which are non-covalently associated with the cell wall of a target cell.

The gene sequences coding for the bacteriocin CBDs according to the present invention can be derived from the corresponding genetic information of the cells, which code for the cell wall binding domains/proteins.

Bacteriophage lysins fall into three categories, glycosidases, amidases, and endopeptidases, depending on the type of chemical bond they cleave within the peptidoglycan. Glycosidases can be further subdivided into the muramidases, glucosaminidases, and transglycosylases. In the present invention, bacteriophage lysins provide at least one of the following enzymatic activities against a peptidoglycan substrate: muramidases, glucosaminidases, N-acetylmuramyl-L-alanine am idase and endopeptidases.

Bacteriophages are not only known to encode and produce lysins, but also so-called tail associated muralytic enzymes (TAMEs), which are likewise capable of hydrolysing bacterial cell walls. While lysins are produced in the final stage of the phage-life cycle to facilitate the release of progeny phage from the host bacterium, TAMEs are, in contrast, produced during the first stage of the process of infection of a host cell. The first stage of the phage infection process comprises the steps of adsorption to and penetration of the host cell, which is mediated using, inter alia, the TAME. Many but not all phages have tails attached to the phage head.

Bacteriophage lysins are structurally composed of two domains, an enzymatic active lytic domain and a cell binding domain. In the present invention, the second portion of the chimeric polypeptide may comprise an amino acid sequence of the lytic domain of a bacteriophage lysine. Excluded from the present invention are bacteriophage tail associated muralytic enzymes (TAMEs). Thus, while the second portion of the chimeric polypeptide of the present invention may comprise an amino acid sequence of the lytic domain of a bacteriophage lysine (endolysin), it is excluded that the lytic domain of a bacteriophage lysin according to the present invention may be a so-called bacteriophage tail associated muralytic enzyme (TAME) as described herein above. In other terms, excluded from the present invention are tail portions of bacteriophages or so-called bacteriophage tail associated muralytic enzymes (TAMEs) exhibiting the activity of hydrolysing bacterial cell walls.

In one aspect of the present invention, a Gram-positive bacterium is preferably a pathogenic Gram-positive bacterium. More preferably, in the present invention a Gram-positive bacterium is a pathogenic *Staphylococcus* bacterium. Still more preferably, in the present invention a pathogenic *Staphylococcus* bacterium is a pathogenic species or sub-species of *Staphylococcus*. In one aspect of the present invention, a pathogenic *Staphylococcus* bacterium is preferably *S. aureus* or MRSA. In another aspect of the present invention, a pathogenic bacterium belonging to the genus *Staphylococcus* is preferably *S. epidermidis* or *S. haemolyticus*. In still another aspect of the present invention, a pathogenic bacterium belonging to the genus *Staphylococcus* is preferably *S. simulans* or *S. saprophyticus*. In a further aspect of the present invention, a pathogenic bacterium belonging to the genus *Staphylococcus* is preferably *S. hyicus* or *S. warneri*. In one aspect, a pathogenic bacterium belonging to the genus *Staphylococcus* is *S. xylosus*.

The above definition applies to all aspects of the present invention, i.e., including the application of a chimeric polypeptide according to the present invention in therapy or prophylaxis as well as the definition of the lytic domain(s) of the EAD(s) and the CBD comprised by the chimeric polypeptide. For example, if the EAD is the lytic domain of a bacteriophage endolysin, wherein the bacteriophage is from a Gram-positive bacterium, the Gram-positive bacterium is preferably a pathogenic Gram-positive bacterium. More preferably, the EAD is the lytic domain of a bacteriophage endolysin, wherein the bacteriophage is from a pathogenic *Staphylococcus* bacterium. Still more preferably, the EAD is the lytic domain of a bacteriophage endolysin, wherein the bacteriophage is from a pathogenic species or sub-species of *Staphylococcus*, specifically from *S. aureus*. Likewise, if the EAD is the lytic domain of a bacteriocin, wherein the bacteriocin is from a Gram-positive bacterium, the Gram-positive bacterium is preferably a pathogenic Gram-positive bacterium. More preferably, the EAD is the lytic domain of a bacteriocin from a pathogenic *Staphylococcus* bacterium. Still more preferably, the EAD is the lytic domain of a bacteriocin from a pathogenic species or sub-species of *Staphylococcus*, specifically from *S. simulans*. Likewise, if the EAD is the lytic domain of a bacterial autolysin from a Gram-positive bacterium, the Gram-positive bacterium is preferably a pathogenic Gram-positive bacterium. More preferably, the EAD is the lytic domain of a bacterial autolysin from a pathogenic *Staphylococcus* bacterium. Still more preferably, the EAD is the lytic domain of a bacterial autolysin from a pathogenic species or sub-species of *Staphylococcus*, specifically from *S. aureus*. Likewise, if the bacteriocin CBD of chimeric polypeptide of the present invention is the bacteriocin CBD of a Gram-positive bacterium, the Gram-positive bacterium is preferably a pathogenic Gram-positive bacterium. More preferably, the bacteriocin CBD is from a pathogenic *Staphylococcus* bacterium. Still more preferably, the bacteriocin CBD is from a pathogenic species or sub-species of *Staphylococcus*, specifically from *S. simulans*.

In one preferred embodiment of the present invention the chimeric polypeptide comprises a first portion and a second portion joined by a linker, wherein said first portion comprises an amino acid sequence of the CBD of lysostaphin, preferably the CBD of SEQ ID NO: 4, and wherein said second portion comprises an amino acid sequence of the CHAP domain of lysK, preferably the CHAP domain of SEQ ID NO: 1 (PRF119 and PRF133). Herein, the CBD of lysostaphin is fused with its N-terminus to the C-terminus of the CHAP domain of lysK. In a preferred embodiment, such a chimeric polypeptide has a MIC value ≤10 µg/ml, preferably ≤1 µg/ml, and more preferably ≤0.1 µg/ml. Furthermore, such a chimeric polypeptide has preferably an MBC (99.99%) value of ≤0.5 µg/ml, preferably ≤0.05 µg/ml.

In a further preferred embodiment of the present invention the chimeric polypeptide comprises a first portion and a second portion joined by a linker, wherein said first portion comprises an amino acid sequence of the CBD of lysostaphin, preferably the CBD of SEQ ID NO: 4, and wherein said second portion comprises an amino acid sequence of the CHAP domain of lysK, preferably the CHAP domain of SEQ ID NO: 1, and an amino acid sequence of the lytic domain of lysostaphin, preferably the lytic domain of SEQ ID NO: 2 (PRF115). Herein, lysostaphin is fused with its N-terminus to the C-terminus of the CHAP domain of lysK. In a preferred embodiment, such a chimeric polypeptide has a MIC value ≤10 µg/ml, preferably ≤1 µg/ml, and more preferably ≤0.1 µg/ml. Furthermore, such a chimeric polypeptide has preferably an MBC (99.99%) value of ≤0.5 µg/ml, preferably ≤0.05 µg/ml.

In a still further preferred embodiment of the present invention the chimeric polypeptide comprises a first portion and a second portion joined by a linker, wherein said first portion comprises an amino acid sequence of the CBD of lysostaphin, preferably the CBD of SEQ ID NO: 4, and wherein said second portion comprises an amino acid sequence of the CHAP domain of lytN, preferably the CHAP domain of SEQ ID NO: 3 (PRF102). Herein, the CBD of lysostaphin is fused with its N-terminus to the C-terminus of the CHAP domain of lytN. In a preferred embodiment, such a chimeric polypeptide has a MIC value ≤10 µg/ml, preferably ≤1 µg/ml, and more preferably ≤0.1 µg/ml. Furthermore, such a chimeric polypeptide has preferably an MBC (99.99%) value of ≤0.5 µg/ml, preferably ≤0.05 µg/ml.

The lytic domain of lysostaphin has a specific lytic action against *Staphylococcus*. In particular, the lytic domain of lysostaphin has glycyl-glycine endopeptidase activity. Accordingly, in one aspect of the present invention the lytic domain of the chimeric polypeptide of the invention is the lytic domain of lysostaphin, which has glycyl-glycine endopeptidase activity. In a preferred embodiment, the lytic domain of the chimeric polypeptide of the present invention is the lytic domain of lysostaphin and thus the chimeric polypeptide is used in prophylaxis or therapy of staphylococcal infections and/or staphylococcal colonisations.

The enzymatic activity of an enzymatic active domain (EAD) of a chimeric polypeptide of the present invention refers to a polypeptide having the activity of lysing a bacterium whose cell wall contains peptidoglycan. Preferably, the bacterium having a cell wall containing peptidoglycan is a Gram-positive bacterium. The nature of peptidoglycan is known to the person skilled in the art as a polymer of amino sugars cross-linked by short peptides which forms a covalent matrix that surrounds the cytoplasmic membrane and constitutes the major skeletal component of the cell wall.

The lytic domains of the present invention can be isolated from nature or can be produced by recombinant or synthetic means. The term "lytic domain" specifically encompasses naturally occurring forms (e.g., alternatively spliced or modified forms) and naturally-occurring variants of the enzyme. In one example, the native sequence enzyme is a mature or full-length polypeptide that is genetically coded for by a gene from a bacteriophage specific for pathogenic staphylococci, preferably methicillin-resistant *Staphylococcus aureus* (MRSA).

A "phage" or "bacteriophage", as used herein, relates to the well-known category of viruses that infect bacteria. Phages include DNA or RNA sequences encapsidated in a protein envelope or coat ("capsid").

The term "CHAP" used in the context of the present invention is known to the person skilled in the art as cysteine, histidine-dependent amidohydrolases/peptidases.

In the present invention, the term "bacterium" preferably describes a "target bacterium", and refers to a bacterium that is bound by a chimeric polypeptide of the present invention and and/or whose growth, survival, or replication is inhibited by the enzymatic activity of the enzymatic active domain (EAD) of the second portion of the chimeric polypeptide according to the present invention. The inhibition of bacterial growth refers to the slowing or stopping of the rate of a bacteria cell's division or cessation of bacterial cell division, or to death of bacteria. The term "target bacterium" specifically includes Gram-positive target bacteria.

"MIC" refers to minimum inhibitory concentration. The MIC value is defined as the lowest concentration of a chimeric polypeptide of the present invention that prevented visible growth of test bacteria. MIC assays were determined by the broth dilution method in a modification of standards of the NCCLS (2003; Methods for dilution antimicriobial susceptibility test for bacteria that grow aerobically; approved standard M7-A6). The concentration of chimeric polypeptides used ranged from 200 μg/ml to 0.00019 μg/ml. Twofold dilutions were performed in Brain Heart Infusion Broth (BHI) supplemented with 0.1% bovine serum albumin (BSA) in a 96-well microtiter plate. Each well was inoculated with $1\times10^5$ CFU/ml *Staphylococcus* diluted from an overnight culture grown in BHI. As a control growth without protein was included. The microtiter plate was incubated at 30° C. for 24 hours. Values were determined by measuring the absorbance at 620 nm in a microplate reader.

"MBC" refers to minimum bactericidal concentration. MBCs for chimeric polypeptides were determined by a modification of the NCCLS standards (1999; Methods for determining bactericidal activity on antimicrobial agents; approved guideline Vol. 19). The concentration of chimeric polypeptides used ranged from 50 μg/ml to 0.00005 μg/ml. Tenfold dilutions were performed in 20 mM Tris/HCl pH 8, 60 mM NaCl, 2 mM $CaCl_2$ supplemented with 1% bovine serum albumin (BSA) in reaction tubes. *Staphylococcus* from an overnight culture in BHI were diluted to a final inoculum of $1\times10^5$ CFU/ml in each tube. A tube containing buffer and BSA but no protein was included as a control. The dilution tubes were incubated at 30° C. for 1 hour. A volume of each sample (100 μl) was plated on LB-Agar plates. The MBC value was defined as the dose of chimeric polypeptide which led to a 3 log or greater drop from the starting bacterial concentration (99.9% killing of the initial inoculum).

"Polypeptide" refers to a molecule comprised of amino acids which correspond to polypeptides encoded by a polynucleotide sequence which is naturally occurring. The polypeptide may include conservative substitutions where the naturally occurring amino acid is replaced by one having similar properties, where such conservative substitutions do not alter the function of the polypeptide (see, for example, Lewin "Genes V" Oxford University Press Chapter 1, pp. 9-13 1994). The terms "polypeptide", "peptide", and "protein" are typically used interchangeably herein to refer to a polymer of amino acid residues. Amino acids may be referred to herein by either their commonly known three letter symbols or by the one-letter symbols recommended by the IUPAC-IUB Biochemical Nomenclature Commission.

The present invention also relates to fragments and variants of the chimeric polypeptides provided herein. Specifically, provided herein are fragments and variants of the CBDs and EADs according to the present invention. In one aspect, provided herein is a variant of the lytic domain of a bacteriophage lysine or endolysin described herein, which has at least 80%, preferably 90%, more preferably 95%, amino acid sequence identity with the polypeptide of SEQ ID NO: 1. In various aspect, provided herein is a variant of the lytic domain of a bacteriophage lysine or endolysin described herein, which has at least 81%, 82%, 83%, 84%, 85%, 86%, 87%, 88%, or 89%, preferably at least 91%, 92%, 93%, or 94%, and more preferably 96%, 97%, 98%, or 99%, amino acid sequence identity with the polypeptide of SEQ ID NO: 1. In another aspect, provided herein is a variant of the lytic domain of a bacteriocin described herein, which has at least 80%, preferably at least 81%, 82%, 83%, 84%, 85%, 86%, 87%, 88%, 89%, 90%, 91%, 92%, 93%, 94%, 95%, 96%, 97%, 98%, or 99%, amino acid sequence identity with the polypeptide of SEQ ID NO: 2. In still another aspect, provided herein is a variant of the lytic domain of a bacterial autolysin described herein, which has at least 80%, preferably at least 81%, 82%, 83%, 84%, 85%, 86%, 87%, 88%, 89%, 90%, 91%, 92%, 93%, 94%, 95%, 96%, 97%, 98%, or 99%, amino acid sequence identity with the polypeptide of SEQ ID NO: 3. In yet a further aspect, provided herein is a variant of the bacteriocin CBD described herein, which has at least 80%, preferably at least 81%, 82%, 83%, 84%, 85%, 86%, 87%, 88%, 89%, 90%, 91%, 92%, 93%, 94%, 95%, 96%, 97%, 98%, or 99%, amino acid sequence identity with the polypeptide of SEQ ID NO: 4. Preferably, these variants have essentially the same biological activity as the corresponding polypeptides of SEQ ID NO: 1, SEQ ID NO: 2, SEQ ID NO: 3, and SEQ ID NO: 4, respectively.

Also provided herein are variants of the chimeric polypeptides of SEQ ID NO: 9, SEQ ID NO: 10, SEQ ID NO: 11, and SEQ ID NO: 15, respectively, wherein each of the variants has at least 80%, preferably at least 81%, 82%, 83%, 84%, 85%, 86%, 87%, 88%, 89%, 90%, 91%, 92%, 93%, 94%, 95%, 96%, 97%, 98%, or 99%, amino acid sequence identity with the corresponding polypeptide of SEQ ID NO: 9, SEQ ID NO: 10, SEQ ID NO: 11, and SEQ ID NO: 15, respectively. In a preferred embodiment, such variants have a MIC value ≤10 μg/ml, preferably ≤1 μg/ml, and more preferably ≤0.1 μg/ml. Furthermore, such variants have preferably an MBC (99.99%) value of ≤0.5 μg/ml, preferably ≤0.05 μg/ml.

"Percent (%) polypeptide sequence identity" with respect to the polypeptide sequences identified herein is defined as the percentage of amino acid residues in a candidate sequence that are identical with the amino acid residues in the specific reference amino acid sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, such as using publicly available computer software such as blast software.

The invention provides variants of the above mentioned chimeric polypeptides, which increase stability and/or activity thereof.

The present invention provides fragments of the chimeric polypeptides of the invention as well as fragments of the CBDs and EADs of the present invention, which still exhibit the biological activity of a chimeric polypeptide or CBD and EAD, respectively, according to the present invention. As used herein, a "fragment" is a polypeptide variant having an amino acid sequence that entirely is the same as part but not all of the amino acid sequence of the reference polypeptide. A fragment may be "free-standing" or comprised as a single continuous region within a larger polypeptide of which they form a part or region. In one aspect, provided herein is a fragment of the amino acid sequence of SEQ ID NO: 1, SEQ ID NO: 2, SEQ ID NO: 3, SEQ ID NO: 4, SEQ ID NO: 9, SEQ ID NO: 10, SEQ ID NO: 11, and SEQ ID NO: 15, respectively, wherein one or more amino acid residues are deleted in the respective amino acid sequence, as long as the fragment exhibits the activity of hydrolysing a bacterial cell wall, preferably a Gram-positive bacterial cell wall. On another aspect, provided herein is a fragment of the amino acid sequence of SEQ ID NO: 4, wherein one or more amino acid residues are deleted in the amino acid sequence of SEQ ID NO: 4, as long as the fragment exhibits the activity of binding to a bacterial cell wall, preferably to the cell wall of a Gram-positive bacterium. In yet another aspect of the present invention, provided herein is a fragment of the amino acid sequence of SEQ ID NO: 9, SEQ ID NO: 10, SEQ ID NO: 11, and SEQ ID NO: 15, respectively, wherein one or more amino acid residues are deleted in the amino acid sequence of the respective polypeptide, as long as the fragment exhibits the activity of inhibition of bacterial growth, including the slowing or stopping of the rate of a bacteria cell's division or cessation of bacterial cell division, or to death of bacteria (killing colonizing bacteria). Preferably, such bacteria are pathogenic bacteria, more preferably pathogenic Gram-positive bacteria.

Biologically active portions of a protein or peptide fragment of the embodiments, as described herein, include polypeptides comprising amino acid sequences sufficiently identical to or derived from the amino acid sequence of the EADs and CBDs according to the present invention, which include fewer amino acids than the full length protein and exhibit the same activity of the corresponding full length protein. A biologically active portion of a protein or protein fragment of the present invention can be a polypeptide which is, for example, 5, 10, 15 or more amino acids less in length than the reference polypeptide sequence. Degradation forms of the polypeptides of this embodiment in a host cell are also provided in some embodiments.

The present invention provides nucleic acids encoding the chimeric polypeptides of the present invention. Furthermore, provided herein are nucleic acids encoding the CBDs and EADs according to the present invention. Also provided are vectors carrying such nucleic acids and host cells transformed or transfected with such vectors.

As used herein, a "nucleic acid" typically refers to deoxyribonucleotide or ribonucleotides polymers (pure or mixed) in single- or double-stranded form. The term may encompass nucleic acids containing nucleotide analogs or modified backbone residues or linkages, which are synthetic, naturally occurring, and non-naturally occurring, which have similar binding, structural, or functional properties as the reference nucleic acid and which are metabolized in a manner similar to the reference nucleotides. Non-limiting examples of such analogs include, without limitation, phosphorothioates, phosphoramidates, methyl phosphonates, chiral-methyl phosphonates, 2-O-methyl ribonucleotides, and peptide-nucleic acids (PNAs). The term nucleic acid may, in some contexts, be used interchangeably with gene, cDNA, mRNA, oligonucleotide, and polynucleotide.

Embodiments of the disclosure include vectors that comprise a polynucleotide or polynucleotides encoding one of the polypeptide sequences described herein, or variants or fragments thereof. Other examples concern host cells that are genetically engineered with vectors of the disclosure and the production of polypeptides of the disclosure by recombinant techniques. Cell-free translation systems can also be employed to produce such proteins using RNAs derived from the DNA constructs of the disclosure.

For recombinant production, host cells can be genetically engineered to incorporate expression systems or portions thereof or polynucleotides of the disclosure. Introduction of a polynucleotide into the host cell can be effected by methods described in many standard laboratory manuals. Representative examples of appropriate hosts include bacterial cells, such as streptococci, staphylococci, enterococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used to produce the polypeptides of the disclosure. Such. vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques. For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the disclosure can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography is also employed for purification. Well-known techniques for refolding protein may be employed to regenerate active conformation when the polypeptide is denatured during isolation and or purification.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of the invention.

The fragments and variants of the polypeptides of the present invention described herein above include proteins or peptides and peptide fragments that are chemically synthesized or prepared by recombinant DNA techniques, or both. Such fragments and variants may interchangeably be described as modified or altered forms of the proteins or peptides of the present invention. In the present invention, peptide variants also include fragments of a polypeptide. When the protein or peptide is produced by chemical synthesis, it is preferably substantially free of chemical precursors or other chemicals, i.e., it is separated from chemical precursors or other chemicals that are involved in the synthesis of the protein. Such polypeptide variants include, for instance, polypeptides wherein one or more amino acid residues are added, or deleted at the N or C terminus of the sequence of SEQ ID NO: 1, SEQ ID NO: 2, SEQ ID NO: 3, SEQ ID NO: 4, SEQ ID NO: 9, SEQ ID NO: 10, SEQ ID NO: 11, or SEQ ID NO: 15. In an embodiment one or more amino acids are substituted, deleted, and/or added to any position(s) in the sequence, or sequence portion thereof.

Variants that are fragments of the polypeptides of the disclosure may be employed for producing the corresponding full-length polypeptide by peptide synthesis; therefore, these variants may be employed as intermediates for producing the full-length polypeptides of embodiments of the disclosure.

Peptide fragments of the present invention may be prepared by any of a number of conventional techniques. Desired peptide fragments may be chemically synthesized. An alternative approach involves generating lytic enzyme fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, EAD or CBD polypeptide fragments of the present invention share the same biological activity with the reference EAD or CBD polypeptide disclosed herein in the sequence listing.

The chimeric polypeptide according to the present invention comprises a linker sequence. In one embodiment, “linker sequence” refers to an amino acid sequence that joins the two portions of the chimeric polypeptide, or fragments or variants thereof. In general, as used herein, a linker is an amino acid sequence that covalently links the polypeptides to form a fusion polypeptide. The linker comprises at least one peptide bond. As appreciated by one of skill in the art, the linker can comprise additional amino acids, such as glycine and other small neutral amino acids.

The present invention also relates to the use of chimeric polypeptides provided by the present invention for the reduction of certain bacterial populations, including methods and compositions for the treatment of various bacterial infections. Thus, the present invention also relates to compositions and formulations comprising chimeric polypeptides according to the present invention and the use of such compositions in prophylaxis or therapy of bacterial diseases, bacterial infections or bacterial colonisations. In one aspect, a composition or formulation of the present invention is a decontamination composition or decontamination formulation. In another aspect, a composition or formulation of the present invention is a decolonisation composition or decolonisation formulation. In yet another aspect, a composition or formulation of the present invention is a disinfectant.

In one aspect of the present invention, the chimeric polypeptides are applied in a method for the treatment or prophylaxis of *Staphylococcus* infections in a subject, in particular for the treatment or prophylaxis of infections by *S. aureus, S. aureus* (MRSA), *S. epidermidis, S. haemolyticus, S. simulans, S. saprophyticus, S. chromogenes, S. hyicus, S. warneri* and/or *S. xylosus*. The subject may be a human subject or an animal, in particular animals used in livestock farming and/or dairy farming such as cattle and pigs. The method of treatment encompasses the application of the chimeric polypeptide of the present invention to the site of infection or site to be prophylactically treated against infection in a sufficient amount.

In particular, the method of treatment may be for the treatment or prophylaxis of infections, in particular by *Staphylococcus aureus* or *S. aureus* (MRSA), of the skin, of soft tissues, of bacteremia and/or endocarditis.

Furthermore, a chimeric polypeptide of the present invention may be used prophylactically as sanitizing agent, in particular before or after surgery, or for example during hemodialysis. Similarly, premature infants and immunocompromised persons, or those subjects with need for prosthetic devices can be treated with a chimeric polypeptide of the present invention, either prophylactically or during acute infection. In the same context, nosocomial infections by *Staphylococcus*, in particular by *S. aureus* or *S. aureus* (MRSA), may be treated prophylactically or during acute phase with a chimeric polypeptide of the present invention. In this embodiment, a chimeric polypeptide of the present invention may be used as a disinfectant also in combination with other ingredients useful in a disinfecting solution like detergents, tensids, solvents, antibiotics, lanthibiotics, or bacteriocins.

In a particular embodiment, a chimeric polypeptide of the present invention is used for medical treatment, if the infection to be treated (or prevented) is caused by multiresistant *Staphylococcus* strains, in particular by strains resistant against vancomycin, linezolid or daptomycin.

A composition as disclosed herein may comprise more than one chimeric polypeptide according to the present invention and/or may comprise one or more additional agents. Non-limiting examples of an additional agent include an enzyme, an antibiotic, an anti-fungal agent, a bactericide, an analgesic, and an anti-inflammatory agent.

A composition or formulation according to the present invention preferably comprises a carrier suitable for delivering the chimeric polypeptide to the site of the bacterial disease, bacterial infection or bacterial colonisation. The compositions and formulations according to the present invention are useful for treating and eliminating bacterial infestations anywhere, including upper respiratory infections, topical and systemic infections, vaginal infections, eye infections, ear infections, infections requiring parenteral treatment, as well as for the elimination of bacteria on any surface, including human skin and mucous membrane, preferably the mucous membrane of the upper respiratory tract, more preferably the mucous membrane of the nasal cavity. The compositions and formulations according to the present invention are particularly useful for the prophylaxis and treatment of upper respiratory infections, skin infections, wounds, burns, vaginal infections, eye infections, intestinal disorders and dental disorders. Specifically, the invention provides the application of the chimeric polypeptides for nasal and/or skin decolonisation of human and animals.

The compositions and formulations comprising a chimeric polypeptide of the present invention as an active ingredient are applied in an effective amount when used in prophylaxis and therapy. The term "effective amount" refers to an amount of an active ingredient sufficient to achieve a desired effect without causing an undesirable side effect. In some cases, it may be necessary to achieve a balance between obtaining a desired effect and limiting the severity of an undesired effect. The amount of active ingredient used will vary depending upon the type of active ingredient and the intended use of the composition and/or formulation of the present invention.

In preferred embodiments, the present invention pertains to chimeric polypeptides of the invention as a prophylactic treatment for preventing those subjects, preferably human subjects, who have possibly been exposed to *Staphylococcus* bacteria, or as a therapeutic treatment for those subjects, preferably human subjects, who have already become ill from an infection with *Staphylococcus* bacteria. The chimeric polypeptides described herein are specific for decolonisation of *Staphylococcus* bacteria, and preferably effectively and efficiently break down the cell wall of *Staphylococcus* bacteria, preferably of methicillin-resistant *S. aureus* (MRSA).

The chimeric polypeptides of the present invention can be formulated according to known methods to prepare pharmaceutically useful compositions, whereby the chimeric polypeptide is combined in admixture with a pharmaceutically acceptable carrier. Compositions, which may be used for the prophylactic and therapeutic treatment of a bacterial infection, preferably a *Staphylococcus* bacteria infection, also includes a means of application (such as a carrier system or an oral delivery mode) to the mucosal lining of the oral and nasal cavity, such that the enzyme is put in the carrier system or oral delivery mode to reach the mucosa lining.

"Carriers" as used herein include pharmaceutically acceptable carriers, excipients or stabilizers, which are non-toxic to the cell or the subject being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween®, polyethylene glycol (PEG), and Pluronics®.

Prior to, or at the time a chimeric polypeptide of the invention is put in the carrier system or oral delivery mode, the enzyme may be in a stabilizing buffer environment for maintaining a suitable pH range, such as between about 5.0 and about 8.0, including a pH of about 5.0, 6.0, 7.0, 8.0 or any pH interval of 0.05 there between, or any interval that is a multiple of 0.05 there between, i.e., including for example pH values of 5.2, 6.5, 7.4, 7.5 and 8.5.

Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions.

Any of the carriers for the chimeric polypeptides of the present invention may be manufactured by conventional means. However, if alcohol is used in the carrier, the enzyme should be in a micelle, liposome, or a "reverse" liposome, to prevent denaturing of the enzyme. Similarly, when the chimeric polypeptide is being placed in the carrier, and the carrier is, or has been heated, such placement should be made after the carrier has cooled somewhat, to avoid heat denaturation of the enzyme. The carrier preferably is sterile. One or more chimeric polypeptides may be added to these substances in a liquid form or in a lyophilized state, whereupon it will be solubilized when it meets a liquid body.

A stabilizing buffer should allow for the optimum activity of the chimeric polypeptide. The buffer may contain a reducing reagent, such as dithiothreitol. The stabilizing buffer may also be or include a metal chelating reagent, such as ethylenediaminetetracetic acid disodium salt, or it may also contain a phosphate or citrate phosphate buffer, or any other buffer.

Pharmaceuticals according to the present invention may include anti-inflammatory agents, anti-viral agents, local anaesthetic agents, corticosteroids, destructive therapy agents, anti-fungals, and/or anti-androgens. Local anaesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. An exemplary concentration for local anaesthetics is about 0.025% to about 5% by weight of the total composition. Anaesthetics such as benzocaine may also be used at a preferred concentration of about 2% to about 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide and are recommended at concentrations of about 0.01% to 1.0% by weight. The concentrations for corticosteroids such as hydrocortisone or methylprednisolone acetate may be from about 0.2% to about 5.0% by weight.

Destructive therapy agents such as salicylic acid or lactic acid may also be used. A concentration of about 2% to about 40% by weight may be used. Cantharidin may be utilized, for example, in a concentration of about 5% to about 30% by weight. Typical anti-fungals that may be used in topical compositions and examples of suitable weight concentrations include: oxiconazole nitrate (0.1% to 5.0%), ciclopirox olamine (0.1% to 5.0%), ketoconazole (0.1% to 5.0%), miconazole nitrate (0.1% to 5.0%), and butoconazole nitrate (0.1% to 5.0%). Other topical agents may be included to address a variety of topical co-infections that may occur as will be appreciated by skilled artisans.

In order to accelerate treatment of the infection, the therapeutic agent may further include at least one complementary agent that can also potentiate the bactericidal activity of the lytic domain of the chimeric polypeptide of the invention. The complementary agent can be erythromycin, clarithromycin, azithromycin, roxithromycin, and other members of the macrolide family, penicillins, cephalosporins, and any combinations thereof in amounts that are effective to synergistically enhance the therapeutic effect of the chimeric polypeptide of the invention. Similarly, other lytic enzymes may be included in the carrier to treat other bacterial infections. Holin proteins may be included in the therapeutic treatment.

In some embodiments, a mild surfactant in an amount effective to potentiate the therapeutic effect of the chimeric polypeptide may be used in or in combination with a therapeutic or prophylactic composition. Suitable mild surfactants include, inter alia, esters of polyoxyethylene sorbitan and fatty acids (Tween series), octylphenoxy polyethoxy ethanol (Triton X series), n-Octyl-β-D-glucopyranoside, n-Octyl-β-D-thioglucopyranoside, n-Decyl-β-D-glucopyranoside, n-Dodecyl-β-D-glucopyranoside, and biologically occurring surfactants, e.g., fatty acids, glycerides, monoglycerides, deoxycholate and esters of deoxycholate.

Therapeutic compositions comprising one or more chimeric polypeptides or variants or fragments thereof can be administered or applied to a subject by any suitable means. Means of application of the chimeric polypeptide(s) (modified or unmodified) of the invention include, but are not limited to, direct, indirect, carrier and special means or any combination of means. Direct application of the chimeric polypeptide may be by nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or any combination of these and similar methods of application. The forms in which the chimeric polypeptide may be administered include but are not limited to powders, sprays, liquids, gels, ointments, and aerosols. It is most probable that exposure to the bacteria will be through the nose. Preferred are sprays, liquids, gels, ointments, and aerosols. Particularly preferred are liquids, gels and ointments. Most preferred are liquids and gels.

When the chimeric polypeptide is introduced directly by use of nasal sprays, nasal drops, nasal ointments, nasal washes, nasal injections, nasal packing, bronchial sprays, oral sprays, or inhalers, the chimeric polypeptide may be in a liquid or gel environment, with the liquid acting as the carrier. A dry anhydrous version of the modified enzyme may be administered by the inhaler and bronchial spray, although a liquid form of delivery may also be used.

Specifically, provided herein are formulation recipes of the chimeric polypeptides of the invention in liquid aqueous matrices.

Specifically, provided herein are formulation recipes of the chimeric polypeptides of the invention in semi-solid matrices for topical applications.

As noted above, the chimeric polypeptide may also be placed in a nasal spray, wherein the spray is the carrier. The nasal spray can be a long acting or timed release spray, and can be manufactured by means well known in the art. An inhalant may also be used, so that the enzyme may reach further down into the bronchial tract, including into the lungs.

Any of the carriers for the chimeric polypeptide may be manufactured by conventional means. However, it is preferred that any mouthwash or similar type products not contain alcohol to prevent denaturing of the enzyme, although enzymes in liposomes and in other protective modes and forms may be used in alcohol.

The dosage and route of administration used in a method of treatment (or prophylaxis) according to the present invention depends on the specific disease/site of infection to be treated. The route of administration may be, for example, in particular embodiments oral, topical, nasopharyngeal, parenteral, intravenous, rectal or any other route of administration.

The effective dosage rates or amounts of the enzyme(s) to treat the infection will depend in part on whether the chimeric polypeptide will be used therapeutically or prophylactically, the duration of exposure of the recipient to the infectious bacteria, the size and weight of the individual, etc. The duration for use of the composition containing the chimeric polypeptide also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of chimeric polypeptide that may provide for an effective amount or dosage of the chimeric polypeptide may be in the range of 10 units/ml to 500,000 units/ml of fluid in the wet or damp environment of the nasal and oral passages, and topically as well and possibly in the range of 10, 20, 30, 40, 50, 60, 70, 80, 90, or 100 units/ml to 50,000 units/ml. Representative values thus include about 200 units/ml, 300 units/ml, 500 units/ml, 1,000 units/ml, 2,500 units/ml, 5,000 units/ml, 10,000 units/ml, 20,000 units/ml, 30,000 units/ml, and 40,000 units/ml. More specifically, time exposure to the active enzyme units may influence the desired concentration of active enzyme units per ml. It should be noted that carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. Thus, the number of dosages will be dependent upon the circumstances and can range from 1 to 4 times per day or more, with durations from one day to multiple weeks.

"Treatment" refers to both therapeutic treatment and prophylactic or preventative measures, wherein the object is to prevent or slow down (lessen) the targeted pathologic condition or disorder, which is a condition or disorder caused by pathological bacteria, specifically Gram-positive pathological bacteria, more specifically staphylococci, more specifically *Staphylococcus aureus*, and most specifically MRSA. Those in need of treatment include those already with the disorder as well as those prone to have the disorder or those for whom the disorder is to be prevented.

"Animal" for purposes of treatment refers to any animal classified as a mammal, including domestic and farm animals, and zoo, sports, or pet animals, such as dogs, cats, cattle, horses, sheep, pigs, goats, rabbits, etc.

The formulations to be used for in vivo administration are preferably sterile. This is readily accomplished by filtration through sterile filtration membranes, prior to or following lyophilisation and reconstitution.

The route of administration is in accordance with known methods. When treating a bacterial exposure or infection, the chimeric polypeptide may be administered in any suitable fashion, including topical administration or through the oral or nasal cavity. For topical application a polypeptide of the present invention may be administered by way of a lotion or plaster. For nasopharyngeal application a chimeric polypeptide according to the present invention may be formulated in saline in order to be applied via a spray to the nose.

Dosages and desired drug concentrations of pharmaceutical compositions of the present invention may vary depending on the particular use envisioned. The determination of the appropriate dosage or route of administration is well within the skill of an ordinary physician.

It is anticipated that different formulations will be effective for different treatment compounds and different disorders, that administration targeting one organ or tissue, for example, may necessitate delivery in a manner different from that to another organ or tissue.

Compositions and formulations for treating topical infections comprise an effective amount of at least one chimeric polypeptide of the present invention produced according to this disclosure and a carrier for delivering at least one chimeric polypeptide to the infected skin. The mode of application for the chimeric polypeptide includes a number of different types and combinations of carriers which include, but are not limited to, an aqueous liquid, an alcohol base liquid, a water soluble gel, a lotion, an ointment, a non-aqueous liquid base, a mineral oil base, a blend of mineral oil and petrolatum, lanolin, liposomes, protein carriers such as serum albumin or gelatin, powdered cellulose carmel, and combinations thereof. In one embodiment, a preferred carrier is an aqueous liquid. In another preferred embodiment, a preferred carrier is an alcohol base liquid. In a further embodiment, a preferred carrier is a water soluble gel. In a further embodiment, a preferred carrier is a non-aqueous liquid base. In a still further embodiment, a preferred carrier is a lotion or an ointment.

A mode of delivery of the carrier containing the therapeutic agent includes, but is not limited to a smear, spray, a time-release patch, a liquid absorbed wipe, and combinations thereof. A preferred mode of delivery of the carrier containing the therapeutic agent is a smear. In one aspect, a preferred mode of delivery of the carrier containing the therapeutic agent is a spray. In one embodiment, a preferred mode of delivery of the carrier containing the therapeutic agent is a liquid absorbed wipe. In a further preferred embodiment, a preferred mode of delivery of the carrier containing the therapeutic agent is a liquid absorbed wipe.

The chimeric polypeptide may be applied to a bandage either directly or in one of the other carriers. The bandages may be sold damp or dry, wherein the chimeric polypeptide is in a lyophilized form on the bandage. This method of application is most effective for the treatment of infected skin.

Preservatives may also be used in this invention and may comprise, for example, about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

All medical applications rely on the effect of the chimeric polypeptides of the present invention to lyse specifically and immediately bacteria, preferably Gram-positive bacteria, more preferably pathogenic Gram-positive bacteria, and still more preferably pathogenic staphylococcal bacteria when encountered. This has an immediate impact on the health status of the treated subject by providing a reduction in pathogenic bacteria and bacterial load and simultaneously relieves the immune system. Thus, the major task a person skilled in the art faces is to formulate the chimeric polypeptides of the present invention accurately for the respective disease to be treated. For this purpose usually the same galenic formulation as employed for conventional medicaments for these applications can be used.

EXAMPLES

Example 1: Cloning of PRF115/Sequence=$CHAP_{lysK}$-Lysostaphin

PRF115 was cloned by "Splicing by overlap extension PCR" (SOE-PCR). In two separate PCR reactions, $CHAP_{lysk}$ and Lysostaphin were amplified, generating overlapping fragments, which are combined to the full length construct in a third PCR. $CHAP_{lysk}$ was amplified using pET14b_Lysk as a template with 5'T7promotor Oligonucleotide and a 3'Oligonucleotide annealing to the 3'-Terminus of the CHAP and containing 15 bases of the 5'-Terminus of Lysostaphin. Lysostaphin was amplified using pET14b_Lysostaphin as a template with a 5'Oligonucleotide annealing to the 5'-Terminus of Lysostaphin and containing 15 bases of the 3'-Terminus of $CHAP_{lysK}$ and 3'T7-Terminator Oligonucleotide. In a third PCR reaction, the overlapping fragments of the first PCRs were used as template and the full length PRF115 gene was amplified using T7-Promotor and T7-Terminator Oligonucleotides. The resulting PCR Product was (i) digested with NcoI and BamHI, ligated into pET14b and pQE60 respectively and transformed into *E. Coli* HMS174 (DE3) and *E. coli* M15 respectively. The sequence was confirmed by fully sequencing the PRF115 gene.

ATGGCGAAAACCCAGGCGGAAATTAACAAACGTCTGGATGCGTATGCGAA
AGGCACCGTGGATAGCCCGTATCGTGTGAAAAAAGCGACCAGCTATGATC
CGAGCTTTGGCGTGATGGAAGCGGGTGCGATTGATGCGGATGGCTATTAT
CACGCGCAGTGCCAGGATCTGATTACCGATTATGTGCTGTGGCTGACCGA
TAACAAAGTGCGTACCTGGGGCAACGCGAAAGATCAGATCAAACAGAGCT
ATGGCACCGGCTTTAAAATCCATGAAAACAAACCGAGCACCGTGCCGAAA
AAAGGCTGGATTGCGGTGTTTACCAGCGGCAGCTATGAACAGTGGGGCCA
TATTGGCATTGTGTATGATGGCGGCAACACCAGCACCTTTACCATTCTGG
AACAGAACTGGAACGGCTATGCGAACAAAAAACCGACCAAACGCGTGGAT
AACTATTATGGCCTGACCCATTTTATTGAAATTCCGGTGAAAGCGGGCAC
CACCGTGAAAAAAGAAACCGCGAAAAAAAGCGCGAGCAAAACCCCGGCGC
CGAAAAAAAAAGCCACCCTGAAAGTGAGCAAAAACCACATCAACTATACG
atgGCGGCGACGCACGAGCATAGCGCCCAGTGGCTGAATAATTACAAAAA
GGGTTACGGTTATGGCCCGTACCCGCTGGGCATCAATGGCGGCATGCACT
ATGGCGTAGACTTCTTTATGAACATTGGCACGCCGGTTAAAGCGATCAGT
TCCGGTAAAATTGTGGAAGCGGGCTGGAGTAACTACGGTGGTGGTAACCA
GATCGGCTTGATTGAAAATGATGGCGTGCACCGTCAGTGGTACATGCATC
TGTCGAAATATAACGTAAAGGTGGGCGACTATGTGAAAGCGGGTCAAATT
ATTGGTTGGTCCGGTAGCACCGGTTATAGTACGGCGCCGCACCTGCATTT
CCAGCGTATGGTGAATAGCTTTTCTAATAGTACCGCACAAGACCCGATGC
CGTTTCTGAAATCCGCGGGTTATGGCAAAGCGGGCGGCACCGTGACTCCG
ACCCCGAACACGGGCTGGAAAACCAACAAGTACGGTACTCTTTACAAAAG
CGAGAGCGCATCTTTTACGCCAAACACGGACATCATCACGCGCACCACCG
GCCCATTTCGCAGCATGCCACAGAGCGGCGTCTTGAAAGCGGGCCAGACC

-continued

ATTCACTACGATGAAGTTATGAAACAGGACGGCCATGTGTGGGTGGGCTA

TACCGGCAACAGCGGCCAGCGTATTTATTTACCGGTTCGCACCTGGAATA

AAAGCACCAATACCTTAGGCGTGTTATGGGGTACCATTAAG

MAKTQAEINKRLDAYAKGTVDSPYRVKKATSYDPSFGVMEAGAIDADGYY

HAQCQDLITDYVLWLTDNKVRTWGNAKDQIKQSYGTGFKIHENKPSTVPK

KGWIAVFTSGSYEQWGHIGIVYDGGNTSTFTILEQNWNGYANKKPTKRVD

NYYGLTHFIEIPV*KAGTTVKKETAKKSASKTPAPKKKATLKVSKNHINYT*

MAATHEHSAQWLNNYKKGYGYGPYPLGINGGMHYGVDFFMNIGTPVKAIS

SGKIVEAGWSNYGGGNQIGLIENDGVHRQWYMHLSKYNVRVGDYVKAGQI

IGWSGSTGYSTAPHLHFQRMVNSFSNSTAQDPMPFLKSAGYGKAGGTVTP

TPNTGWKTNKYGTLYKSESASFTPNTDIITRTTGPFRSMPQSGVLKAGQT

IHYDEVMKQDGHVWVGYTGNSGQRIYLPVRTWNKSTNTLGVLWGTIK

Example 2: Cloning of PRF119/ Sequence=$CHAP_{lysK}$-$CBD_{lysostaphin}$

PRF119 was cloned by "Splicing by overlap extension PCR" (SOE-PCR). In two separate PCR reactions, CHAP-lysk and CBDLysostaphin were amplified, generating an overlapping area on both fragments. $CHAP_{lysk}$ was amplified using pET14b_Lysk as a template with 5'T7-promotor Oligonucleotide and a 3'Oligonucleotide annealing to the 3'-Terminus of the CHAP that contained 15 bases of the 5'-Terminus of the CBD lysostaphin. $CBD_{lysostaphin}$ was amplified using pET14b_Lysostaphin as a template with a 5'Oligonucleotide annealing to the 5'-Terminus of the $CBD_{lysostaphin}$ and containing 15 bases of the 3'-Terminus of CHAPlysK and 3'T7-Terminator Oligonucleotide. In a second PCR reaction, the overlapping fragments of the first PCRs were used as template and the full length PRF119 gene was amplified using T7Promotor and T7-Terminator Oligonucleotides. The resulting PCR Product was (i) digested with NcoI and BamHI, ligated into pET14b and pQE60 respectively and transformed into E. *Coli* HMS174 (DE3) and *E. coli* M15 respectively. The sequence was confirmed by fully sequencing the PRF119 gene.

ATGGCGAAAACCCAGGCGGAAATTAACAAACGTCTGGATGCGTATGCGAA

AGGCACCGTGGATAGCCCGTATCGTGTGAAAAAAGCGACCAGCTATGATC

CGAGCTTTGGCGTGATGGAAGCGGGTGCGATTGATGCGGATGGCTATTAT

CACGCGCAGTGCCAGGATCTGATTACCGATTATGTGCTGTGGCTGACCGA

TAACAAAGTGCGTACCTGGGGCAACGCGAAAGATCAGATCAAACAGAGCT

ATGGCACCGGCTTTAAAATCCATGAAAACAAACCGAGCACCGTGCCGAAA

AAAGGCTGGATTGCGGTGTTTACCAGCGGCAGCTATGAACAGTGGGGCCA

TATTGGCATTGTGTATGATGGCGGCAACACCAGCACCTTTACCATTCTGG

AACAGAACTGGAACGGCTATGCGAACAAAAAACCGACCAAACGCGTGGAT

AACTATTATGGCCTGACCCATTTTATTGAAATTCCGGTGATGTCTAATAG

CACCGCGCAGGACCCGATGCCGTTCTTGAAGTCGGCGGGCTATGGCAAAG

CAGGCGGCACCGTGACTCCGACCCCGAACACGGGCTGGAAAACCAACAAG

TACGGTACTCTTTACAAAAGCGAGAGCGCATCTTTTACGCCAAACACGGA

-continued

CATCATCACGCGCACCACCGGCCCATTTCGCAGCATGCCACAGAGCGGCG

TCTTGAAAGCGGGCCAGACCATTCACTACGATGAAGTTATGAAACAGGAC

GGCCATGTGTGGGTGGGCTATACCGGCAACAGCGGCCAGCGTATTTATTT

ACCGGTTCGCACCTGGAATAAAAGCACCAATACCTTAGGCGTGTTATGGG

GTACCATTAAGTAA

MAKTQAEINKRLDAYAKGTVDSPYRVKKATSYDPSFGVMEAGAIDADGYY

HAQCQDLITDYVLWLTDNKVRTWGNAKDQIKQSYGTGFKIHENKPSTVPK

KGWIAVFTSGSYEQWGHIGIVYDGGNTSTFTILEQNWNGYANKKPTKRVD

NYYGLTHFIEIPVMSNSTAQDPMPFLKSAGYGKAGGTVTPTPNTGWKTNK

YGTLYKSESASFTPNTDIITRTTGPFRSMPQSGVLKAGQTIHYDEVMKQD

GHVWVGYTGNSGQRIYLPVRTWNKSTNTLGVLWGTIK

Example 3: Cloning of PRF102/ Sequence=$CHAP_{lytN}$-$CBD_{lysostaphin}$

PRF102 was cloned by "Splicing by overlap extension PCR" (SOE-PCR). In two separate PCR reactions, CHAP-lytN and CBD lysostaphin were amplified, generating an overlapping area on both fragments.

$CHAP_{lytN}$ was amplified using pET14b_$CHAP_{lytN}$ as a template with 5'T7Promotor Oligonucleotide and an 3'Oligonucleotide annealing to the 3'-Terminus of the $CHAP_{lytN}$ that contained 15 bases of the 5'-Terminus of the $CBD_{lysostaphin}$. $CBD_{lysostaphin}$ was amplified using pET14b_Lysostaphin as a template with a 5'Oligonucleotide annealing to the 5'-Terminus of the $CBD_{lysostaphin}$ and containing 15 bases of the 3'-Terminus of $CHAP_{lytN}$ and 3'T7Terminator Oligonucleotide. In a second PCR reaction, the overlapping fragments of the first PCRs were used as template and the full length PRF102 gene was amplified using T7Promotor and T7Terminator Oligonucleotides. The resulting PCR Product was (i) digested with NcoI and BamHI, ligated into pET14b and pQE60 respectively and transformed into E. *Coli* HMS174(DE3) and *E. coli* M15 respectively. The sequence was confirmed by fully sequencing the PRF102 gene.

ATGGCGAGTACATTAAATTATTTGAAAACATTAGAGAATAGAGGATGGGA

TTTCGACGGTAGTTATGGATGGCAATGTTTCGATTTAGTTAATGTATATT

GGAATCATCTTTATGGTCATGGATTAAAAGGATATGGAGCTAAAGATATA

CCATATGCAAATAATTTTAATAGTGAAGCTAAAATTTATCACAACACACC

AACTTTCAAAGCTGAACCTGGGGACTTAGTGGTTTTTAGTGGAAGATTTG

GTGGAGGATATGGTCATACAGCTATTGTCTTAAATGGTGATTATGATGGA

AAATTAATGAAGTTCCAAAGTTTAGATCAAAACTGGAATAATGGTGGATG

GCGTAAAGCAGAGGTTGCACATAAAGTTGTTCATAATTATGAAAATGATA

TGATTTTTATTAGACCATTTAAAAAAGCAATGTCTAATAGCACCGCGCAG

GACCCGATGCCGTTCTTGAAGTCGGCGGGCTATGGCAAAGCAGGCGGCAC

CGTGACTCCGACCCCGAACACGGGCTGGAAAACCAACAAGTACGGTACTC

TTTACAAAAGCGAGAGCGCATCTTTTACGCCAAACACGGACATCATCACG

-continued

CGCACCACCGGCCCATTTCGCAGCATGCCACAGAGCGGCGTCTTGAAAGC

GGGCCAGACCATTCACTACGATGAAGTTATGAAACAGGACGGCCATGTGT

GGGTGGGCTATACCGGCAACAGCGGCCAGCGTATTTATTTACCGGTTCGC

ACCTGGAATAAAAGCACCAATACCTTAGGCGTGTTATGGGGTACCATTAA

GTAA

MASTLNYLKTLENRGWDFDGSYGWQCFDLVNVYWNHLYGHGLKGYGAKDI

PYANNFNSEAKIYHNTPTFKAEPGDLVVFSGRFGGGYGHTAIVLNGDYDG

KLMKFQSLDQNWNNGGWRKAEVAHKVVHNYENDMIFIRPFKKAMSNSTAQ

DPMPFLKSAGYGKAGGTVTPTPNTGWKTNKYGTLYKSESASFTPNTDIIT

RTTGPFRSMPQSGVLKAGQTIHYDEVMKQDGHVWVGYTGNSGQRIYLPVR

TWNKSTNTLGVLWGTIK

Example 4: MIC Data

Determination of MIC values was performed in 96-well plates (Nunc, Nunclon Δ). Concentrations from 200 μg/ml to 0.00019 μg/ml of protein were mixed with $2\times10^4$ cfu/well of *Staphylococcus* cell culture in BHI medium. The plate was incubated at 30° C. and optical density was measured at 600 nm after 24 hours. MIC values correlate to the lowest protein concentration at which no growth of bacteria was observed. The results are shown in Table 1.

TABLE 1

| Minimal inhibitory concentration (MIC) | |
|---|---|
| Protein | MIC value for *S. aureus* (μg/ml) |
| PRF115 | 0.059 |
| PRF119 | 0.39 |
| PRF102 | 9.95 |
| PRF133 | 0.1 |
| LysK | 87.5 |

Example 5: MBC Data

A *Staphylococcus* culture with an optical density of 0.1 was grown in BHI medium at 37° C. to an optical density of 0.8 (correlates to $10^8$ Cfu/ml). Cells were harvested (4,500 rpm, 4° C., 10 minutes) and resuspended in the same volume of (i) sterile 20 mM Tris pH 7.5, 60 mM NaCl, 2 mM $CaCl_2$, 0.1% BSA. The culture was then diluted to $10^5$ Cfu/ml in sterile 20 mM Tris pH 7.5, 60 mM NaCl, 2 mM $CaCl_2$, 0.1% BSA. The cells were mixed with protein concentrations from 50 μg/ml to 0.00005 μg/ml and incubated at 30° C. for 1 hour. Dilutions from $10^5$ to $10^2$ Cfu/ml were plated on LB-agar plates, incubated over night at 37° C. and colonies were counted. MBC (99.99%) values correlate to the lowest protein concentration at which a four log reduction of bacterial cells are measured. The result is shown in Table 2.

TABLE 2

| Minimal bactericidal concentration (MBC) | |
|---|---|
| Protein | MBC (99.99%) value for *S. aureus* (μg/ml) |
| PRF102 | 0.05 |

Example 6: Log Reduction in Mucin

A *Staphylococcus* culture with an optical density of 0.1 was grown in BHI medium at 37° C. to an optical density of 0.8 (correlates to $10^8$ Cfu/ml). Cells were harvested (4,500 rpm, 4° C., 10 minutes) and resuspended in the same volume of (i) sterile 20 mM Tris pH 7.5, 60 mM NaCl, 2 mM $CaCl_2$ and (ii) sterile 20 mM Tris pH 7.5, 60 mM NaCl, 2 mM $CaCl_2$ plus 2% bovine Mucin. Samples of both preparations were mixed with 0.1 mg/ml protein and dilutions were plated on Mannitol Salt Agar plates after 1-10 minutes. Plates were incubated at 37° C. and colonies were counted. The results are shown in Table 3.

TABLE 3

| log reduction of *S. aureus* cells in mucin | |
|---|---|
| Protein | Log reduction |
| PRF119 | 5 |
| PRF102 | 5 |
| PRF133 | 6.5 |

Example 7: Stability Data

Thermal Stability was assayed by a photometric thermal kinetic assay. Protein solutions of 0.1 mg/ml in desired buffer were heated in quartz cuvettes 1° C. per minute from 20° C. to 95° C. and aggregation was followed by measuring light dispersion at 360 nm. The temperature at which aggregation starts was determined as thermal changeover. The results are shown in Table 4.

TABLE 4

| Thermal stability | |
|---|---|
| Protein | Thermal Changeover |
| PRF115 | 61° C. |
| PRF119 | 54° C. |
| PRF102 | 34° C. |
| PRF133 | 55° C. |

Long term stability was determined by incubating high concentrations of protein at −20° C., 4° C., 25° C. and 37° C. Samples were taken either weekly, daily or after hours and centrifuged. Residual protein concentration was determined and the lytic activity by following the decrease of optical density in a photometric assay. Stability was followed up to 1 year. Samples were also analyzed by SDS-PAGE to observe proteolytic stability. The results after storage for 38 days are shown in Table 4.1.

TABLE 4.1

| Long-term stability | |
|---|---|
| Protein | Residual activity after 38 days at 37° C. |
| PRF119 | 5% |
| PRF133 | 85% |

Example 8: Selectivity *S. aureus* vs. *S. epidermidis* vs. *S. haemolyticus*

Selectivity was measured by determining the MIC value for the different *Staphylococcus* strains (see Example 4). The results are shown in Table 5.

TABLE 5

| Selectivity (MIC values in µg/ml) | | | |
|---|---|---|---|
| Protein | *S. aureus* | *S. epidermidis* | *S. haemolyticus* |
| PRF115 | 0.059 | 0.18 | 67 |
| PRF119 | 0.39 | 3.125 | n.d. |
| PRF102 | 9.95 | 12.5 | 12.5 |

Example 9: In Vivo Experiment (Topical Application)

Samples of untreated skin flora were taken using LB-Agar and *Staphylococcus*-specific Mannitol Salt Agar contact plates from the forearm. Skin areals of 2×2 cm were treated with 10-20 µg protein by dispersing 100-200 µl of a hydrogel containing 0.1 mg/ml of protein (PRF-102). After 2 minutes, samples were again taken by LB and MSA contact plates. Additional, skin areals were treated with a common disinfectant (Sterilium, Fa. Bode) and samples were taken after 1 minute. The plates were incubated at 37° C. over night. Residual colonies found on MSA Agar after treatment with proteingel were identified as *Staphylococcus epidermidis*. The results are shown in FIG. 1. Topical application of a chimeric polypeptide of the present invention results in successful decolonisation of skin flora, as shown by the LB- and MSA-Agar plates reflecting the samples taken from human skin treated with 10-20 µg protein containing Hydrogel.

Example 10: Formulation 2.5% Hydroxyethylcellulose (HEC), containing a buffer substance, e.g. 25-50 mM sodium phosphate or Tris/HCl pH 5.5 or 7.5, and stabilizing ingredients, e.g. 25 mM $CaCl_2$, 25 mM Citrate and 300 mM L-arginine. HEC was swollen in sterile buffer at low temperature until a homogenous gel has formed. The protein was then dispersed in the readily swollen gel. Efficacy was shown for example by treating *Staphylococcus aureus* on Agar plates. $10^5$ cells were plated on LB agar plates and shortly after the plate was dried, 100 µl of a hydrogel containing 0.1 mg/ml protein were dispersed on one half of the plate. The plate was then incubated at 37° C. over night. The results are shown in FIG. 2. Application of a chimeric polypeptide of the present invention results in successful decolonisation of *Staphylococcus aureus*, as shown by the upper half of the Agar plate of FIG. 2B treated with gel containing 10 µg PRF102.

Although specific embodiments have been disclosed herein in some detail, this has been done solely for the purposes of describing various features and aspects of embodiments, and is not intended to be limiting with respect to the scope of these embodiments. It is contemplated that various substitutions, alterations, and/or modifications, including but not limited to those implementation variations which may have been suggested herein, may be made to the disclosed embodiments without departing from the spirit and scope of the embodiments as defined by the appended claims which follow.

Example 11: Cloning of PRF133/Sequence=$CHAP_{lysK}$-Synthetic Linker-$CBD_{lysostaphin}$ PRF133 was cloned by "Splicing by overlap extension PCR" (SOE-PCR). In two separate PCR reactions, $CHAP_{lysk}$ and $CBD_{lysostaphin}$ were amplified, generating an overlapping area on both fragments. $CHAP_{lysk}$ was amplified using pET14b_LysK as a template with 5'-T7-promotor Oligonucleotide and a 3'Oligonucleotide annealing to the 3'-Terminus of the CHAP that contained 33 bases of a synthetic linker sequence. $CBD_{lysostaphin}$ was amplified using pET14b_Lysostaphin as a template with a 5'Oligonucleotide annealing 67 bases downstream from the 5'-Terminus of $CBD_{lysostaphin}$ and containing 33 bases of a synthetic linker sequence and 3'-T7-Terminator Oligonucleotide. In a second PCR reaction, the overlapping fragments of the first PCRs were used as template and the full length PRF133 was amplified using T7-Promotor and T7-Terminator Oligonucleotides. The resulting PCR Product was digested with NcoI and BamHI, ligated into pET14b and pQE60 respectively. The sequence was confirmed by fully sequencing the PRF133 gene.

ATGGCGAAAACCCAGGCGGAAATTAACAAACGTCTGGATGCGTATGCGAA

AGGCACCGTGGATAGCCCGTATCGTGTGAAAAAAGCGACCAGCTATGATC

CGAGCTTTGGCGTGATGGAAGCGGGTGCGATTGATGCGGATGGCTATTAT

CACGCGCAGTGCCAGGATCTGATTACCGATTATGTGCTGTGGCTGACCGA

TAACAAAGTGCGTACCTGGGGCAACGCGAAAGATCAGATCAAACAGAGCT

ATGGCACCGGCTTTAAAATCCATGAAAACAAACCGAGCACCGTGCCGAAA

AAAGGCTGGATTGCGGTGTTTACCAGCGGCAGCTATGAACAGTGGGGCCA

TATTGGCATTGTGTATGATGGCGGCAACACCAGCACCTTTACCATTCTGG

AACAGAACTGGAACGGCTATGCGAACAAAAAACCGACCAAACGCGTGGAT

AACTATTATGGCCTGACCCATTTTATTGAAATTCCGGTG*GGCGGTAGCAA*

*ACCTGGAGGCACGAAGCCGGGTGGAAGCAAACCAGGATCG*ACCGTGACTC

CGACCCCGAACACGGGCTGGAAAACCAACAAGTACGGTACTCTTTACAAA

AGCGAGAGCGCATCTTTTACGCCAAACACGGACATCATCACGCGCACCAC

CGGCCCATTTCGCAGCATGCCACAGAGCGGCGTCTTGAAAGCGGGCCAGA

CCATTCACTACGATGAAGTTATGAAACAGGACGGCCATGTGTGGGTGGGC

TATACCGGCAACAGCGGCCAGCGTATTTATTTACCGGTTCGCACCTGGAA

TAAAAGCACCAATACCTTAGGCGTGTTATGGGGTACCATTAAGTAA

MAKTQAEINKRLDAYAKGTVDSPYRVKKATSYDPSFGVMEAGAIDADGYY

HAQCQDLITDYVLWLTDNKVRTWGNAKDQIKQSYGTGFKIHENKPSTVPK

KGWIAVFTSGSYEQWGHIGIVYDGGNTSTFTILEQNWNGYANKKPTKRVD

NYYGLTHFIEIPV*GGSKPGGTKPGGSKPGS*TVTPTPNTGWKTNKYGTLYK

SESASFTPNTDIITRTTGPFRSMPQSGVLKAGQTIHYDEVMKQDGHVWVG

YTGNSGQRIYLPVRTWNKSTNTLGVLWGTIK

Example 12: pH-Dependent Activity of PRF119

Figure 3:
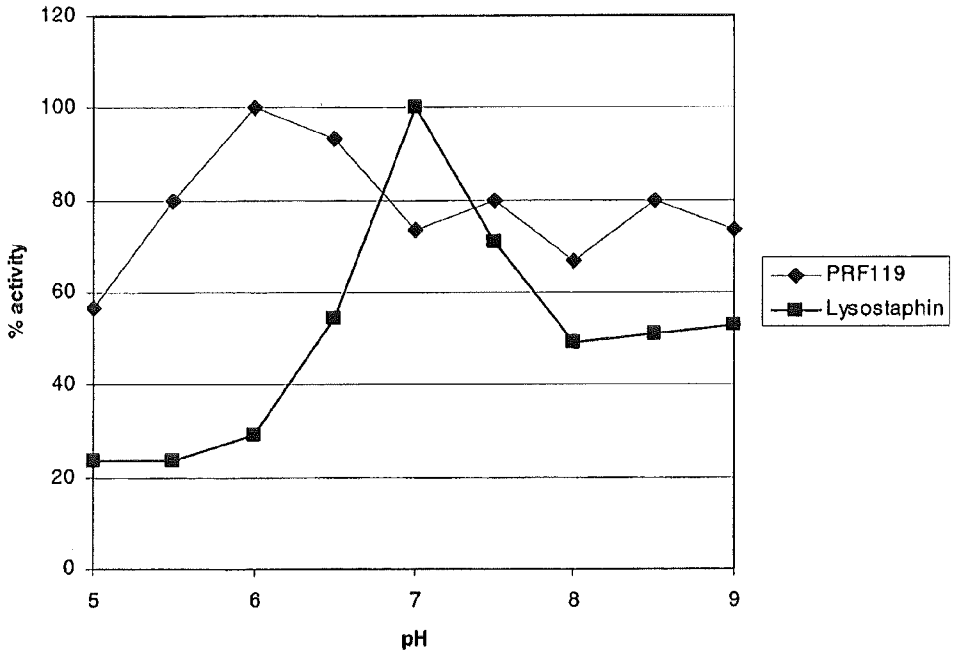
FIG. 3 shows pH-dependent activity of PRF119 on a *Staphylococcus aureus* culture.

A *Staphylococcus aureus* culture with an optical density of 0.1 was grown in BHI medium at 37° C. to an optical density of 1. Cells were harvested (4,500 rpm, 4° C., 10 minutes) and resupended in 10 mM Acetate, 10 mM Tris, 10 mM Borate, 60 mM NaCl, 2 mM $CaCl_2$, pH ranging from 5-9. After adding 5 μg/ml protein, decrease of optical density per minute was followed at 30° C. FIG. 3 shows the results.

REFERENCES

1. Borysowski J. et al., 2006, Exp. Biol. Med. 231: 366-377.
2. UK patent application GB 2 255 561 A (Nov. 11, 1992).
3. Nelson D. et al., 2001, PNAS 98(7):4107-4112.
4. Rashel M. et al., 2007, J. Infect. Dis. 196(8):1237-1247.
5. U.S. Pat. No. 5,997,862 (Dec. 7, 1999).
6. Takác M. and U. Bläsi, 2005, Antimicrob. Agents Chemother. 49(7):2934-2940.
7. Navarre W. et al., 1999, J. Biol. Chem. 274(22):15847-15856.
8. Sass P. and G. Bierbaum, 2007, Appl. Environ. Microbiol. 73(1):347-352.
9. O'Flaherty S. et al., 2005, J. Bacteriol. 187(20):7161-7164.
10. WO 2008/001342 (Jan. 3, 2008)
11. Becker S. et al., 2008, FEMS Micobiol. Lett. 287(2): 185-191.
12. Horgan M. et al., 2009, Appl. Environ. Microbiol. 75(3):872-874.
13. Kumar Jaspal K., 2008, Appl. Microbiol. Biotechnol. 80:555-561.
14. Kokai-Kun J. F. et al., 2007, J. Antimicrob. Chemother. 60(5):1051-1059.
15. Kusuma C. et al., 2007, Antimicrob. Agents Chemother. ≤1(2):475-482.
16. DeHart H. P. et al., 1995, Appl. Environ. Microbiol. 61(4):1475-1479.
17. Ehlert K. et al., 1997, J. Bacteriol. 197(23):7573-7576.
18. Strandén A. M. et al., 1997, J. Bacteriol. 197(1):9-16.
19. Diaz E. et al., 1990, Proc. Natl. Acad. Sci. USA 87:8125-8129.
20. Croux C. et al., 1993, Mol. Microbiol. 9(5):1019-1025.
21. Donovan D. M. et al., 2006, Appl. Environ. Microbiol. 72(4):2988-2996.
22. WO 2007/130655 A2 (Nov. 15, 2007)

SEQUENCE LISTING

SEQ ID NO: 1: amino acid sequence of the CHAP domain of lysK (163 amino acid residues; translated sequence of the nucleotide sequence of SEQ ID NO: 5; origin: bacteriophage phiK)

```
MAKTQAEINKRLDAYAKGTVDSPYRVKKATSYDPSFGVMEAGAIDADGYY

HAQCQDLITDYVLWLTDNKVRTWGNAKDQIKQSYGTGFKIHENKPSTVPK

KGWIAVFTSGSYEQWGHIGIVYDGGNTSTFTILEQNWNGYANKKPTKRVD

NYYGLTHFIEIPV
```

SEQ ID NO: 2: amino acid sequence of the lytic domain of lysostaphin (124 amino acid residues; translated sequence of the nucleotide sequence of SEQ ID NO: 6; origin: *Staphylococcus simulans*)

```
MAATHEHSAQWLNNYKKGYGYGPYPLGINGGMHYGVDFFMNIGTPVKA

ISSGKIVEAGWSNYGGGNQIGLIENDGVHRQWYMHLSKYNVKVGDYVK

AGQIIGWSGSTGYSTAPHLHFQRMVNSF
```

SEQ ID NO: 3: amino acid sequence of the CHAP domain of lytN (143 amino acid residues; translated sequence of the nucleotide sequence of SEQ ID NO: 7; origin: *Staphylococcus aureus*)

```
MASTLNYLKTLENRGWDFDGSYGWQCFDLVNVYWNHLYGHGLKGYGAK

DIPYANNFNSEAKIYHNTPTFKAEPGDLVVFSGRFGGGYGHTAIVLNG

DYDGKLMKFQSLDQNWNNGGWRKAEVAHKVVHNYENDMIFIRPFKKA
```

SEQ ID NO: 4: amino acid sequence of the CBD of lysostaphin (123 amino acid residues; translated sequence of nucleotide sequence of SEQ ID NO: 8; origin: *Staphylococcus simulans*)

```
SNSTAQDPMPFLKSAGYGKAGGTVTPTPNTGWKTNKYGTLYKSESASF

TPNTDIITRTTGPFRSMPQSGVLKAGQTIHYDEVMKQDGHVWVGYTGN

SGQRIYLPVRTWNKSTNTLGVLWGTIK
```

SEQ ID NO: 5: nucleotide sequence of the CHAP domain of lysK (489 nucleotides; origin: bacteriophage phiK)

```
ATGGCGAAAACCCAGGCGGAAATTAACAAACGTCTGGATGCGTATGCGAAAGGCACCGTGGATAG

CCCGTATCGTGTGAAAAAAGCGACCAGCTATGATCCGAGCTTTGGCGTGATGGAAGCGGGTGCGA

TTGATGCGGATGGCTATTATCACGCGCAGTGCCAGGATCTGATTACCGATTATGTGCTGTGGCTG

ACCGATAACAAAGTGCGTACCTGGGGCAACGCGAAAGATCAGATCAAACAGAGCTATGGCACCGG

CTTTAAAATCCATGAAAACAAACCGAGCACCGTGCCGAAAAAAGGCTGGATTGCGGTGTTTACCA

GCGGCAGCTATGAACAGTGGGGCCATATTGGCATTGTGTATGATGGCGGCAACACCAGCACCTTT

ACCATTCTGGAACAGAACTGGAACGGCTATGCGAACAAAAAACCGACCAAACGCGTGGATAACTA

TTATGGCCTGACCCATTTTATTGAAATTCCGGTG
```

SEQ ID NO: 6: nucleotide sequence of the lytic domain of lysostaphin (372 nucleotides; origin: *Staphylococcus simulans*)

ATGGCGGCGACGCACGAGCATAGCGCCCAGTGGCTGAATAATTACAAAAAGGGTTACGGTTATGG

CCCGTACCCGCTGGGCATCAATGGCGGCATGCACTATGGCGTAGACTTCTTTATGAACATTGGCA

CGCCGGTTAAAGCGATCAGTTCCGGTAAAATTGTGGAAGCGGGCTGGAGTAACTACGGTGGTGGT

AACCAGATCGGCTTGATTGAAAATGATGGCGTGCACCGTCAGTGGTACATGCATCTGTCGAAATA

TAACGTAAAGGTGGGCGACTATGTGAAAGCGGGTCAAATTATTGGTTGGTCCGGTAGCACCGGTT

ATAGTACGGCGCCGCACCTGCATTTCCAGCGTATGGTGAATAGCTTT

SEQ ID NO: 7: nucleotide sequence of the CHAP domain of lytN (429 nucleotides; origin: *Staphylococcus aureus*)

ATGGCGAGTACATTAAATTATTTGAAAACATTAGAGAATAGAGGATGGGATTTCGACGGTAGTTA

TGGATGGCAATGTTTCGATTTAGTTAATGTATATTGGAATCATCTTTATGGTCATGGATTAAAAG

GATATGGAGCTAAAGATATACCATATGCAAATAATTTTAATAGTGAAGCTAAAATTTATCACAAC

ACACCAACTTTCAAAGCTGAACCTGGGGACTTAGTGGTTTTTAGTGGAAGATTTGGTGGAGGATA

TGGTCATACAGCTATTGTCTTAAATGGTGATTATGATGGAAAATTAATGAAGTTCCAAAGTTTAG

ATCAAAACTGGAATAATGGTGGATGGCGTAAAGCAGAGGTTGCACATAAAGTTGTTCATAATTAT

GAAAATGATATGATTTTTATTAGACCATTTAAAAAAGCA

SEQ ID NO: 8: nucleotide sequence of the CBD of lysostaphin (369 nucleotides; origin: *Staphylococcus simulans*)

TCTAATAGCACCGCGCAGGACCCGATGCCGTTCTTGAAGTCGGCGGGCTATGGCAAAGCAGGCGG

CACCGTGACTCCGACCCCGAACACGGGCTGGAAAACCAACAAGTACGGTACTCTTTACAAAAGCG

AGAGCGCATCTTTTACGCCAAACACGGACATCATCACGCGCACCACCGGCCCATTTCGCAGCATG

CCACAGAGCGGCGTCTTGAAAGCGGGCCAGACCATTCACTACGATGAAGTTATGAAACAGGACGG

CCATGTGTGGGTGGGCTATACCGGCAACAGCGGCCAGCGTATTTATTTACCGGTTCGCACCTGGA

ATAAAAGCACCAATACCTTAGGCGTGTTATGGGGTACCATTAAG

SEQ ID NO: 9: amino acid sequence of clone PRF115 (447 amino acid residues; translated sequence of nucleotide sequence of SEQ ID NO: 12; origin: bacteriophage phiK and *Staphylococcus simulans*)

MAKTQAEINKRLDAYAKGTVDSPYRVKKATSYDPSFGVMEAGAIDADGYYHAQCQDLITDYVLWL

TDNKVRTWGNAKDQIKQSYGTGFKIHENKPSTVPKKGWIAVFTSGSYEQWGHIGIVYDGGNTSTF

TILEQNWNGYANKKPTKRVDNYYGLTHFIEIPVKAGTTVKKETAKKSASKTPAPKKKATLKVSKN

HINYTMAATHEHSAQWLNNYKKGYGYGPYPLGINGGMHYGVDFFMNIGTPVKAISSGKIVEAGWS

NYGGGNQIGLIENDGVHRQWYMHLSKYNVKVGDYVKAGQIIGWSGSTGYSTAPHLHFQRMVNSFS

NSTAQDPMPFLKSAGYGKAGGTVTPTPNTGWKTNKYGTLYKSESASFTPNTDIITRTTGPFRSMP

QSGVLKAGQTIHYDEVMKQDGHVWVGYTGNSGQRIYLPVRTWNKSTNTLGVLWGTIK

SEQ ID NO: 10: amino acid sequence of clone PRF119 (287 amino acid residues; translated sequence of nucleotide sequence of SEQ ID NO: 13; origin: bacteriophage phiK and *Staphylococcus simulans*)

```
MAKTQAEINKRLDAYAKGTVDSPYRVKKATSYDPSFGVMEAGAIDADGYYHAQCQDLITDYVLWL
TDNKVRTWGNAKDQIKQSYGTGFKIHENKPSTVPKKGWIAVFTSGSYEQWGHIGIVYDGGNTSTF
TILEQNWNGYANKKPTKRVDNYYGLTHFIEIPVMSNSTAQDPMPFLKSAGYGKAGGTVTPTPNTG
WKTNKYGTLYKSESASFTPNTDIITRTTGPFRSMPQSGVLKAGQTIHYDEVMKQDGHVWVGYTGN
SGQRIYLPVRTWNKSTNTLGVLWGTIK
```

SEQ ID NO: 11: amino acid sequence of clone PRF102 (267 amino acid residues; translated sequence of nucleotide sequence of SEQ ID NO: 14; origin: *Staphylococcus simulans* and *Staphylococcus aureus*)

```
MASTLNYLKTLENRGWDFDGSYGWQCFDLVNVYWNHLYGHGLKGYGAKDIPYANNFNSEAKIYHN
TPTFKAEPGDLVVFSGRFGGGYGHTAIVLNGDYDGKLMKFQSLDQNWNNGGWRKAEVAHKVVHNY
ENDMIFIRPFKKAMSNSTAQDPMPFLKSAGYGKAGGTVTPTPNTGWKTNKYGTLYKSESASFTPN
TDIITRTTGPFRSMPQSGVLKAGQTIHYDEVMKQDGHVWVGYTGNSGQRIYLPVRTWNKSTNTLG
VLWGTIK
```

SEQ ID NO: 12: nucleotide sequence of clone PRF115 (1,341 nucleotides; origin: bacteriophage phiK and *Staphylococcus simulans*)

```
ATGGCGAAAACCCAGGCGGAAATTAACAAACGTCTGGATGCGTATGCGAAAGGCACCGTGGATAG
CCCGTATCGTGTGAAAAAAGCGACCAGCTATGATCCGAGCTTTGGCGTGATGGAAGCGGGTGCGA
TTGATGCGGATGGCTATTATCACGCGCAGTGCCAGGATCTGATTACCGATTATGTGCTGTGGCTG
ACCGATAACAAAGTGCGTACCTGGGGCAACGCGAAAGATCAGATCAAACAGAGCTATGGCACCGG
CTTTAAAATCCATGAAAACAAACCGAGCACCGTGCCGAAAAAAGGCTGGATTGCGGTGTTTACCA
GCGGCAGCTATGAACAGTGGGGCCATATTGGCATTGTGTATGATGGCGGCAACACCAGCACCTTT
ACCATTCTGGAACAGAACTGGAACGGCTATGCGAACAAAAAACCGACCAAACGCGTGGATAACTA
TTATGGCCTGACCCATTTTATTGAAATTCCGGTGAAAGCGGGCACCACCGTGAAAAAAGAAACCG
CGAAAAAAAGCGCGAGCAAAACCCCGGCGCCGAAAAAAAAAGCCACCCTGAAAGTGAGCAAAAAC
CACATCAACTATACGATGGCGGCGACGCACGAGCATAGCGCCCAGTGGCTGAATAATTACAAAAA
GGGTTACGGTTATGGCCCGTACCCGCTGGGCATCAATGGCGGCATGCACTATGGCGTAGACTTCT
TTATGAACATTGGCACGCCGGTTAAAGCGATCAGTTCCGGTAAAATTGTGGAAGCGGGCTGGAGT
AACTACGGTGGTGGTAACCAGATCGGCTTGATTGAAAATGATGGCGTGCACCGTCAGTGGTACAT
GCATCTGTCGAAATATAACGTAAAGGTGGGCGACTATGTGAAAGCGGGTCAAATTATTGGTTGGT
CCGGTAGCACCGGTTATAGTACGGCGCCGCACCTGCATTTCCAGCGTATGGTGAATAGCTTTTCT
AATAGTACCGCACAAGACCCGATGCCGTTTCTGAAATCCGCGGGTTATGGCAAAGCGGGCGGCAC
CGTGACTCCGACCCCGAACACGGGCTGGAAAACCAACAAGTACGGTACTCTTTACAAAAGCGAGA
GCGCATCTTTTACGCCAAACACGGACATCATCACGCGCACCACCGGCCCATTTCGCAGCATGCCA
CAGAGCGGCGTCTTGAAAGCGGGCCAGACCATTCACTACGATGAAGTTATGAAACAGGACGGCCA
TGTGTGGGTGGGCTATACCGGCAACAGCGGCCAGCGTATTTATTTACCGGTTCGCACCTGGAATA
AAAGCACCAATACCTTAGGCGTGTTATGGGGTACCATTAAG
```

SEQ ID NO: 13: nucleotide sequence of clone PRF119 (864 nucleotides; origin: bacteriophage phiK and *Staphylococcus simulans*)

ATGGCGAAAACCCAGGCGGAAATTAACAAACGTCTGGATGCGTATGCGAAAGGCACCGTGGATAG
CCCGTATCGTGTGAAAAAAGCGACCAGCTATGATCCGAGCTTTGGCGTGATGGAAGCGGGTGCGA
TTGATGCGGATGGCTATTATCACGCGCAGTGCCAGGATCTGATTACCGATTATGTGCTGTGGCTG
ACCGATAACAAAGTGCGTACCTGGGGCAACGCGAAAGATCAGATCAAACAGAGCTATGGCACCGG
CTTTAAAATCCATGAAAACAAACCGAGCACCGTGCCGAAAAAAGGCTGGATTGCGGTGTTTACCA
GCGGCAGCTATGAACAGTGGGGCCATATTGGCATTGTGTATGATGGCGGCAACACCAGCACCTTT
ACCATTCTGGAACAGAACTGGAACGGCTATGCGAACAAAAAACCGACCAAACGCGTGGATAACTA
TTATGGCCTGACCCATTTTATTGAAATTCCGGTGATGTCTAATAGCACCGCGCAGGACCCGATGC
CGTTCTTGAAGTCGGCGGGCTATGGCAAAGCAGGCGGCACCGTGACTCCGACCCCGAACACGGGC
TGGAAAACCAACAAGTACGGTACTCTTTACAAAAGCGAGAGCGCATCTTTTACGCCAAACACGGA
CATCATCACGCGCACCACCGGCCCATTTCGCAGCATGCCACAGAGCGGCGTCTTGAAAGCGGGCC
AGACCATTCACTACGATGAAGTTATGAAACAGGACGGCCATGTGTGGGTGGGCTATACCGGCAAC
AGCGGCCAGCGTATTTATTTACCGGTTCGCACCTGGAATAAAAGCACCAATACCTTAGGCGTGTT
ATGGGGTACCATTAAGTAA

SEQ ID NO: 14: nucleotide sequence of clone PRF102 (804 nucleotides; origin: *Staphylococcus simulans* and *Staphylococcus aureus*)

ATGGCGAGTACATTAAATTATTTGAAAACATTAGAGAATAGAGGATGGGATTTCGACGGTAGTTA
TGGATGGCAATGTTTCGATTTAGTTAATGTATATTGGAATCATCTTTATGGTCATGGATTAAAAG
GATATGGAGCTAAAGATATACCATATGCAAATAATTTTAATAGTGAAGCTAAAATTTATCACAAC
ACACCAACTTTCAAAGCTGAACCTGGGGACTTAGTGGTTTTTAGTGGAAGATTTGGTGGAGGATA
TGGTCATACAGCTATTGTCTTAAATGGTGATTATGATGGAAAATTAATGAAGTTCCAAAGTTTAG
ATCAAAACTGGAATAATGGTGGATGGCGTAAAGCAGAGGTTGCACATAAAGTTGTTCATAATTAT
GAAAATGATATGATTTTTATTAGACCATTTAAAAAAGCAATGTCTAATAGCACCGCGCAGGACCC
GATGCCGTTCTTGAAGTCGGCGGGCTATGGCAAAGCAGGCGGCACCGTGACTCCGACCCCGAACA
CGGGCTGGAAAACCAACAAGTACGGTACTCTTTACAAAAGCGAGAGCGCATCTTTTACGCCAAAC
ACGGACATCATCACGCGCACCACCGGCCCATTTCGCAGCATGCCACAGAGCGGCGTCTTGAAAGC
GGGCCAGACCATTCACTACGATGAAGTTATGAAACAGGACGGCCATGTGTGGGTGGGCTATACCG
GCAACAGCGGCCAGCGTATTTATTTACCGGTTCGCACCTGGAATAAAAGCACCAATACCTTAGGC
GTGTTATGGGGTACCATTAAGTA

SEQ ID NO: 15: amino acid sequence of clone PRF133 (281 amino acid residues; translated sequence of nucleotide sequence of SEQ ID NO: 16; origin: bacteriophage phiK and *Staphylococcus simulans*)

MAKTQAEINKRLDAYAKGTVDSPYRVKKATSYDPSFGVMEAGAIDADGYY

HAQCQDLITDYVLWLTDNKVRTWGNAKDQIKQSYGTGFKIHENKPSTVPK

-continued

KGWIAVFTSGSYEQWGHIGIVYDGGNTSTFTILEQNWNGYANKKPTKRVD

NYYGLTHFIEIPVGGSKPGGTKPGGSKPGSTVTPTPNTGWKTNKYGTLYK

SESASFTPNTDIITRTTGPFRSMPQSGVLKAGQTIHYDEVMKQDGHVWVG

YTGNSGQRIYLPVRTWNKSTNTLGVLWGTIK

SEQ ID NO: 16: nucleotide sequence of clone PRF133 (846 nucleotides; origin: bacteriophage phiK and *Staphylococcus simulans*)

ATGGCGAAAACCCAGGCGGAAATTAACAAACGTCTGGATGCGTATGCGAAAGGCACCGTGGATAG

CCCGTATCGTGTGAAAAAAGCGACCAGCTATGATCCGAGCTTTGGCGTGATGGAAGCGGGTGCGA

TTGATGCGGATGGCTATTATCACGCGCAGTGCCAGGATCTGATTACCGATTATGTGCTGTGGCTG

ACCGATAACAAAGTGCGTACCTGGGGCAACGCGAAAGATCAGATCAAACAGAGCTATGGCACCGG

CTTTAAAATCCATGAAAACAAACCGAGCACCGTGCCGAAAAAAGGCTGGATTGCGGTGTTTACCA

GCGGCAGCTATGAACAGTGGGGCCATATTGGCATTGTGTATGATGGCGGCAACACCAGCACCTTT

ACCATTCTGGAACAGAACTGGAACGGCTATGCGAACAAAAAACCGACCAAACGCGTGGATAACTA

TTATGGCCTGACCCATTTTATTGAAATTCCGGTGGGCGGTAGCAAACCTGGAGGCACGAAGCCGG

GTGGAAGCAAACCAGGATCGACCGTGACTCCGACCCCGAACACGGGCTGGAAAACCAACAAGTAC

GGTACTCTTTACAAAAGCGAGAGCGCATCTTTTACGCCAAACACGGACATCATCACGCGCACCAC

CGGCCCATTTCGCAGCATGCCACAGAGCGGCGTCTTGAAAGCGGGCCAGACCATTCACTACGATG

AAGTTATGAAACAGGACGGCCATGTGTGGGTGGGCTATACCGGCAACAGCGGCCAGCGTATTTAT

TTACCGGTTCGCACCTGGAATAAAAGCACCAATACCTTAGGCGTGTTATGGGGTACCATTAAGTA

A

The invention claimed is:

1. A chimeric polypeptide comprising a first portion and a second portion joined by a linker, wherein
   a) said first portion consisting of the amino acid sequence of a bacteriocin cell binding domain (CBD), wherein the CBD has greater than 90% amino acid sequence identity with the CBD of the chimeric polypeptide of SEQ ID NO: 15 which extends from amino acid residues 181 to 281 of SEQ ID NO: 15; and
   b) said second portion comprises an amino acid sequence of at least one enzymatic active domain (EAD) wherein the EAD comprises the lytic domain of a bacteriophage endolysin, and has greater than 90% amino acid sequence identity with the EAD of the chimeric polypeptide of SEQ ID NO: 15,
   wherein the chimeric polypeptide has bacterial cell wall lytic activity.

2. The chimeric polypeptide of claim 1, wherein the linker comprises at least one peptide bond.

3. A nucleic acid molecule encoding the chimeric polypeptide of claim 1.

4. A composition comprising the chimeric polypeptide of claim 1.

5. A topical formulation comprising the chimeric polypeptide of claim 1.

6. The topical formulation of claim 5, which is in the form of a bioadhesive, a medicated plaster, or a skin patch.

7. A method of performing prophylaxis or therapy in a mammal comprising administering to the mammal in need thereof the chimeric polypeptide of claim 1.

8. A method of treating or preventing a bacterial disease, a bacterial infection or bacterial colonization in a mammal comprising administering to the mammal in need thereof the chimeric polypeptide of claim 1.

9. The method of claim 8, wherein the chimeric polypeptide of claim 1 is formulated in a pharmaceutical composition.

10. The method of claim 8, wherein the polypeptide
   a) decreases the occurrence or severity of a local or systemic bacterial disease or bacterial infection, or
   b) prevents, reduces, or eliminates bacterial colonization.

11. The method of claim 8, wherein the bacterial disease, bacterial infection or bacterial colonization are caused by gram-positive bacteria.

12. The method of claim 11, wherein the gram-positive bacteria is selected from the group consisting of *Staphylococcus*, *Staphylococcus aureus*, and methicillin-resistant *Staphylococcus aureus* (MRSA).

13. The method of claim 8, wherein the bacterial disease, bacterial infection or bacterial colonization is a bacterial disease, a bacterial infection or bacterial colonization of the skin or a mucous membrane, wherein the mucous membrane is of the upper respiratory tract, or of the nasal cavity.

14. The chimeric polypeptide of claim 1, further comprising a pharmaceutically acceptable carrier.

15. The chimeric polypeptide of claim 14, wherein the carrier is aqueous, and is selected from the group consisting of a cream, a gel, a lotion, and a paste.

16. The chimeric polypeptide of claim 1, wherein the chimeric polypeptide has bacterial cell wall lytic activity.

17. The chimeric polypeptide of claim 1, comprising the CBD and the EAD of the chimeric polypeptide of SEQ ID NO: 15, wherein the CBD extends from amino acid residues 181 to 281 of SEQ ID NO: 15, and the EAD extends from amino acid residues 1 to 163 of SEQ ID NO: 15.

18. The chimeric polypeptide of claim 1, comprising the amino acid sequence of the chimeric polypeptide of SEQ ID NO: 15.

* * * * *

SEQUENCE LISTING

<160> NUMBER OF SEQ ID NOS: 16

<210> SEQ ID NO 1
<211> LENGTH: 163
<212> TYPE: PRT
<213> ORGANISM: Bacteriophage phi-K

<400> SEQUENCE: 1

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys

```
    130                 135                 140

Pro Thr Lys Arg Val Asp Asn Tyr Tyr Gly Leu Thr His Phe Ile Glu
145                 150                 155                 160

Ile Pro Val


<210> SEQ ID NO 2
<211> LENGTH: 124
<212> TYPE: PRT
<213> ORGANISM: Staphylococcus simulans

<400> SEQUENCE: 2

Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe
        115                 120


<210> SEQ ID NO 3
<211> LENGTH: 143
<212> TYPE: PRT
<213> ORGANISM: Staphylococcus aureus

<400> SEQUENCE: 3

Met Ala Ser Thr Leu Asn Tyr Leu Lys Thr Leu Glu Asn Arg Gly Trp
1               5                   10                  15

Asp Phe Asp Gly Ser Tyr Gly Trp Gln Cys Phe Asp Leu Val Asn Val
            20                  25                  30

Tyr Trp Asn His Leu Tyr Gly His Gly Leu Lys Gly Tyr Gly Ala Lys
        35                  40                  45

Asp Ile Pro Tyr Ala Asn Asn Phe Asn Ser Glu Ala Lys Ile Tyr His
    50                  55                  60

Asn Thr Pro Thr Phe Lys Ala Glu Pro Gly Asp Leu Val Val Phe Ser
65                  70                  75                  80

Gly Arg Phe Gly Gly Gly Tyr Gly His Thr Ala Ile Val Leu Asn Gly
                85                  90                  95

Asp Tyr Asp Gly Lys Leu Met Lys Phe Gln Ser Leu Asp Gln Asn Trp
            100                 105                 110

Asn Asn Gly Gly Trp Arg Lys Ala Glu Val Ala His Lys Val Val His
        115                 120                 125

Asn Tyr Glu Asn Asp Met Ile Phe Ile Arg Pro Phe Lys Lys Ala
    130                 135                 140


<210> SEQ ID NO 4
<211> LENGTH: 124
<212> TYPE: PRT
<213> ORGANISM: Staphylococcus simulans
```

<400> SEQUENCE: 4

Met Ser Asn Ser Thr Ala Gln Asp Pro Met Pro Phe Leu Lys Ser Ala
1               5                   10                  15

Gly Tyr Gly Lys Ala Gly Gly Thr Val Thr Pro Thr Pro Asn Thr Gly
            20                  25                  30

Trp Lys Thr Asn Lys Tyr Gly Thr Leu Tyr Lys Ser Glu Ser Ala Ser
        35                  40                  45

Phe Thr Pro Asn Thr Asp Ile Ile Thr Arg Thr Thr Gly Pro Phe Arg
    50                  55                  60

Ser Met Pro Gln Ser Gly Val Leu Lys Ala Gly Gln Thr Ile His Tyr
65                  70                  75                  80

Asp Glu Val Met Lys Gln Asp Gly His Val Trp Val Gly Tyr Thr Gly
                85                  90                  95

Asn Ser Gly Gln Arg Ile Tyr Leu Pro Val Arg Thr Trp Asn Lys Ser
            100                 105                 110

Thr Asn Thr Leu Gly Val Leu Trp Gly Thr Ile Lys
        115                 120

<210> SEQ ID NO 5
<211> LENGTH: 489
<212> TYPE: DNA
<213> ORGANISM: Bacteriophage phi-K

<400> SEQUENCE: 5
atggcgaaaa cccaggcgga aattaacaaa cgtctggatg cgtatgcgaa aggcaccgtg 60
gatagcccgt atcgtgtgaa aaaagcgacc agctatgatc cgagctttgg cgtgatggaa 120
gcgggtgcga ttgatgcgga tggctattat cacgcgcagt gccaggatct gattaccgat 180
tatgtgctgt ggctgaccga taacaaagtg cgtacctggg gcaacgcgaa agatcagatc 240
aaacagagct atggcaccgg ctttaaaatc catgaaaaca aaccgagcac cgtgccgaaa 300
aaaggctgga ttgcggtgtt taccagcggc agctatgaac agtggggcca tattggcatt 360
gtgtatgatg gcggcaacac cagcaccttt accattctgg aacagaactg gaacggctat 420
gcgaacaaaa aaccgaccaa acgcgtggat aactattatg gcctgaccca ttttattgaa 480
attccggtg 489

<210> SEQ ID NO 6
<211> LENGTH: 372
<212> TYPE: DNA
<213> ORGANISM: Staphylococcus simulans

<400> SEQUENCE: 6
atggcggcga cgcacgagca tagcgcccag tggctgaata attacaaaaa gggttacggt 60
tatggcccgt acccgctggg catcaatggc ggcatgcact atggcgtaga cttctttatg 120
aacattggca cgccggttaa agcgatcagt tccggtaaaa ttgtggaagc gggctggagt 180
aactacggtg gtggtaacca gatcggcttg attgaaaatg atggcgtgca ccgtcagtgg 240
tacatgcatc tgtcgaaata taacgtaaag gtgggcgact atgtgaaagc gggtcaaatt 300
attggttggt ccggtagcac cggttatagt acggcgccgc acctgcattt ccagcgtatg 360
gtgaatagct tt 372

<210> SEQ ID NO 7
<211> LENGTH: 429
<212> TYPE: DNA

<213> ORGANISM: Staphylococcus aureus

<400> SEQUENCE: 7
atggcgagta cattaaatta tttgaaaaca ttagagaata gaggatggga tttcgacggt 60
agttatggat ggcaatgttt cgatttagtt aatgtatatt ggaatcatct ttatggtcat 120
ggattaaaag gatatggagc taaagatata ccatatgcaa ataattttaa tagtgaagct 180
aaaatttatc acaacacacc aactttcaaa gctgaacctg gggacttagt ggtttttagt 240
ggaagatttg gtggaggata tggtcataca gctattgtct taaatggtga ttatgatgga 300
aaattaatga agttccaaag tttagatcaa aactggaata atggtggatg gcgtaaagca 360
gaggttgcac ataaagttgt tcataattat gaaaatgata tgatttttat tagaccattt 420
aaaaaagca 429

<210> SEQ ID NO 8
<211> LENGTH: 372
<212> TYPE: DNA
<213> ORGANISM: Staphylococcus simulans

<400> SEQUENCE: 8
atgtctaata gcaccgcgca ggacccgatg ccgttcttga agtcggcggg ctatggcaaa 60
gcaggcggca ccgtgactcc gaccccgaac acgggctgga aaaccaacaa gtacggtact 120
ctttacaaaa gcgagagcgc atcttttacg ccaaacacgg acatcatcac gcgcaccacc 180
ggcccatttc gcagcatgcc acagagcggc gtcttgaaag cgggccagac cattcactac 240
gatgaagtta tgaaacagga cggccatgtg tgggtgggct ataccggcaa cagcggccag 300
cgtatttatt taccggttcg cacctggaat aaaagcacca ataccttagg cgtgttatgg 360
ggtaccatta ag 372

<210> SEQ ID NO 9
<211> LENGTH: 447
<212> TYPE: PRT
<213> ORGANISM: Artificial sequence
<220> FEATURE:
<223> OTHER INFORMATION: bacteriophage phiK and Staphylococcus simulans

<400> SEQUENCE: 9

Met Ala Lys Thr Gln Ala Glu Ile Asn Lys Arg Leu Asp Ala Tyr Ala
1 5 10 15

Lys Gly Thr Val Asp Ser Pro Tyr Arg Val Lys Lys Ala Thr Ser Tyr
20 25 30

Asp Pro Ser Phe Gly Val Met Glu Ala Gly Ala Ile Asp Ala Asp Gly
35 40 45

Tyr Tyr His Ala Gln Cys Gln Asp Leu Ile Thr Asp Tyr Val Leu Trp
50 55 60

Leu Thr Asp Asn Lys Val Arg Thr Trp Gly Asn Ala Lys Asp Gln Ile
65 70 75 80

Lys Gln Ser Tyr Gly Thr Gly Phe Lys Ile His Glu Asn Lys Pro Ser
85 90 95

Thr Val Pro Lys Lys Gly Trp Ile Ala Val Phe Thr Ser Gly Ser Tyr
100 105 110

Glu Gln Trp Gly His Ile Gly Ile Val Tyr Asp Gly Gly Asn Thr Ser
115 120 125

Thr Phe Thr Ile Leu Glu Gln Asn Trp Asn Gly Tyr Ala Asn Lys Lys
130 135 140

-continued

Pro Thr Lys Arg Val Asp Asn Tyr Tyr Gly Leu Thr His Phe Ile Glu
145 150 155 160

Ile Pro Val Lys Ala Gly Thr Thr Val Lys Lys Glu Thr Ala Lys Lys
165 170 175

Ser Ala Ser Lys Thr Pro Ala Pro Lys Lys Lys Ala Thr Leu Lys Val
180 185 190

Ser Lys Asn His Ile Asn Tyr Thr Met Ala Ala Thr His Glu His Ser
195 200 205

Ala Gln Trp Leu Asn Asn Tyr Lys Lys Gly Tyr Gly Tyr Gly Pro Tyr
210 215 220

Pro Leu Gly Ile Asn Gly Gly Met His Tyr Gly Val Asp Phe Phe Met
225 230 235 240

Asn Ile Gly Thr Pro Val Lys Ala Ile Ser Ser Gly Lys Ile Val Glu
245 250 255

Ala Gly Trp Ser Asn Tyr Gly Gly Gly Asn Gln Ile Gly Leu Ile Glu
260 265 270

Asn Asp Gly Val His Arg Gln Trp Tyr Met His Leu Ser Lys Tyr Asn
275 280 285

Val Lys Val Gly Asp Tyr Val Lys Ala Gly Gln Ile Ile Gly Trp Ser
290 295 300

Gly Ser Thr Gly Tyr Ser Thr Ala Pro His Leu His Phe Gln Arg Met
305 310 315 320

Val Asn Ser Phe Ser Asn Ser Thr Ala Gln Asp Pro Met Pro Phe Leu
325 330 335

Lys Ser Ala Gly Tyr Gly Lys Ala Gly Gly Thr Val Thr Pro Thr Pro
340 345 350

Asn Thr Gly Trp Lys Thr Asn Lys Tyr Gly Thr Leu Tyr Lys Ser Glu
355 360 365

Ser Ala Ser Phe Thr Pro Asn Thr Asp Ile Ile Thr Arg Thr Thr Gly
370 375 380

Pro Phe Arg Ser Met Pro Gln Ser Gly Val Leu Lys Ala Gly Gln Thr
385 390 395 400

Ile His Tyr Asp Glu Val Met Lys Gln Asp Gly His Val Trp Val Gly
405 410 415

Tyr Thr Gly Asn Ser Gly Gln Arg Ile Tyr Leu Pro Val Arg Thr Trp
420 425 430

Asn Lys Ser Thr Asn Thr Leu Gly Val Leu Trp Gly Thr Ile Lys
435 440 445

<210> SEQ ID NO 10
<211> LENGTH: 287
<212> TYPE: PRT
<213> ORGANISM: Artificial sequence
<220> FEATURE:
<223> OTHER INFORMATION: bacteriophage phiK and Staphylococcus simulans

<400> SEQUENCE: 10

Met Ala Lys Thr Gln Ala Glu Ile Asn Lys Arg Leu Asp Ala Tyr Ala
1 5 10 15

Lys Gly Thr Val Asp Ser Pro Tyr Arg Val Lys Lys Ala Thr Ser Tyr
20 25 30

Asp Pro Ser Phe Gly Val Met Glu Ala Gly Ala Ile Asp Ala Asp Gly
35 40 45

Tyr Tyr His Ala Gln Cys Gln Asp Leu Ile Thr Asp Tyr Val Leu Trp
50 55 60

-continued

```
Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Met Ser Asn Ser Thr Ala Gln Asp Pro Met Pro Phe Leu
                165                 170                 175

Lys Ser Ala Gly Tyr Gly Lys Ala Gly Gly Thr Val Thr Pro Thr Pro
            180                 185                 190

Asn Thr Gly Trp Lys Thr Asn Lys Tyr Gly Thr Leu Tyr Lys Ser Glu
        195                 200                 205

Ser Ala Ser Phe Thr Pro Asn Thr Asp Ile Ile Thr Arg Thr Thr Gly
    210                 215                 220

Pro Phe Arg Ser Met Pro Gln Ser Gly Val Leu Lys Ala Gly Gln Thr
225                 230                 235                 240

Ile His Tyr Asp Glu Val Met Lys Gln Asp Gly His Val Trp Val Gly
                245                 250                 255

Tyr Thr Gly Asn Ser Gly Gln Arg Ile Tyr Leu Pro Val Arg Thr Trp
            260                 265                 270

Asn Lys Ser Thr Asn Thr Leu Gly Val Leu Trp Gly Thr Ile Lys
        275                 280                 285


<210> SEQ ID NO 11
<211> LENGTH: 267
<212> TYPE: PRT
<213> ORGANISM: Artificial sequence
<220> FEATURE:
<223> OTHER INFORMATION: Staphylococcus simulans and Staphylococcus
      aureus

<400> SEQUENCE: 11

Met Ala Ser Thr Leu Asn Tyr Leu Lys Thr Leu Glu Asn Arg Gly Trp
1               5                   10                  15

Asp Phe Asp Gly Ser Tyr Gly Trp Gln Cys Phe Asp Leu Val Asn Val
            20                  25                  30

Tyr Trp Asn His Leu Tyr Gly His Gly Leu Lys Gly Tyr Gly Ala Lys
        35                  40                  45

Asp Ile Pro Tyr Ala Asn Asn Phe Asn Ser Glu Ala Lys Ile Tyr His
    50                  55                  60

Asn Thr Pro Thr Phe Lys Ala Glu Pro Gly Asp Leu Val Val Phe Ser
65                  70                  75                  80

Gly Arg Phe Gly Gly Gly Tyr Gly His Thr Ala Ile Val Leu Asn Gly
                85                  90                  95

Asp Tyr Asp Gly Lys Leu Met Lys Phe Gln Ser Leu Asp Gln Asn Trp
            100                 105                 110

Asn Asn Gly Gly Trp Arg Lys Ala Glu Val Ala His Lys Val Val His
        115                 120                 125

Asn Tyr Glu Asn Asp Met Ile Phe Ile Arg Pro Phe Lys Lys Ala Met
    130                 135                 140
```

```
Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Trp
                165                 170                 175

Lys Thr Asn Lys Tyr Gly Thr Leu Tyr Lys Ser Glu Ser Ala Ser Phe
            180                 185                 190

Thr Pro Asn Thr Asp Ile Ile Thr Arg Thr Thr Gly Pro Phe Arg Ser
        195                 200                 205

Met Pro Gln Ser Gly Val Leu Lys Ala Gly Gln Thr Ile His Tyr Asp
    210                 215                 220

Glu Val Met Lys Gln Asp Gly His Val Trp Val Gly Tyr Thr Gly Asn
225                 230                 235                 240

Ser Gly Gln Arg Ile Tyr Leu Pro Val Arg Thr Trp Asn Lys Ser Thr
                245                 250                 255

Asn Thr Leu Gly Val Leu Trp Gly Thr Ile Lys
            260                 265
```

<210> SEQ ID NO 12
<211> LENGTH: 1341
<212> TYPE: DNA
<213> ORGANISM: Artificial sequence
<220> FEATURE:
<223> OTHER INFORMATION: bacteriophage phiK and Staphylococcus simulans

<400> SEQUENCE: 12

```
atggcgaaaa cccaggcgga aattaacaaa cgtctggatg cgtatgcgaa aggcaccgtg     60

gatagcccgt atcgtgtgaa aaaagcgacc agctatgatc cgagctttgg cgtgatggaa    120

gcgggtgcga ttgatgcgga tggctattat cacgcgcagt gccaggatct gattaccgat    180

tatgtgctgt ggctgaccga taacaaagtg cgtacctggg gcaacgcgaa agatcagatc    240

aaacagagct atggcaccgg ctttaaaatc catgaaaaca aaccgagcac cgtgccgaaa    300

aaaggctgga ttgcggtgtt taccagcggc agctatgaac agtggggcca tattggcatt    360

gtgtatgatg gcggcaacac cagcaccttt accattctgg aacagaactg gaacggctat    420

gcgaacaaaa aaccgaccaa acgcgtggat aactattatg gcctgaccca ttttattgaa    480

attccggtga aagcgggcac caccgtgaaa aaagaaaccg cgaaaaaaag cgcgagcaaa    540

accccggcgc cgaaaaaaaa agccaccctg aaagtgagca aaaaccacat caactatacg    600

atggcggcga cgcacgagca tagcgcccag tggctgaata attacaaaaa gggttacggt    660

tatggcccgt acccgctggg catcaatggc ggcatgcact atggcgtaga cttctttatg    720

aacattggca cgccggttaa agcgatcagt tccggtaaaa ttgtggaagc gggctggagt    780

aactacggtg gtggtaacca gatcggcttg attgaaaatg atggcgtgca ccgtcagtgg    840

tacatgcatc tgtcgaaata taacgtaaag gtgggcgact atgtgaaagc gggtcaaatt    900

attggttggt ccggtagcac cggttatagt acggcgccgc acctgcattt ccagcgtatg    960

gtgaatagct tttctaatag taccgcacaa gacccgatgc cgtttctgaa atccgcgggt   1020

tatggcaaag cgggcggcac cgtgactccg accccgaaca cgggctggaa aaccaacaag   1080

tacggtactc tttacaaaag cgagagcgca tcttttacgc caaacacgga catcatcacg   1140

cgcaccaccg gcccatttcg cagcatgcca cagagcggcg tcttgaaagc gggccagacc   1200

attcactacg atgaagttat gaaacaggac ggccatgtgt gggtgggcta taccggcaac   1260

agcggccagc gtatttattt accggttcgc acctggaata aaagcaccaa taccttaggc   1320
```

gtgttatggg gtaccattaa g 1341

<210> SEQ ID NO 13
<211> LENGTH: 861
<212> TYPE: DNA
<213> ORGANISM: Artificial sequence
<220> FEATURE:
<223> OTHER INFORMATION: bacteriophage phiK and Staphylococcus simulans

<400> SEQUENCE: 13
atggcgaaaa cccaggcgga aattaacaaa cgtctggatg cgtatgcgaa aggcaccgtg 60
gatagcccgt atcgtgtgaa aaaagcgacc agctatgatc cgagctttgg cgtgatggaa 120
gcgggtgcga ttgatgcgga tggctattat cacgcgcagt gccaggatct gattaccgat 180
tatgtgctgt ggctgaccga taacaaagtg cgtacctggg gcaacgcgaa agatcagatc 240
aaacagagct atggcaccgg ctttaaaatc catgaaaaca aaccgagcac cgtgccgaaa 300
aaaggctgga ttgcggtgtt taccagcggc agctatgaac agtggggcca tattggcatt 360
gtgtatgatg gcggcaacac cagcaccttt accattctgg aacagaactg gaacggctat 420
gcgaacaaaa aaccgaccaa acgcgtggat aactattatg gcctgaccca ttttattgaa 480
attccggtga tgtctaatag caccgcgcag gacccgatgc cgttcttgaa gtcggcgggc 540
tatggcaaag caggcggcac cgtgactccg accccgaaca cgggctggaa aaccaacaag 600
tacggtactc tttacaaaag cgagagcgca tcttttacgc caaacacgga catcatcacg 660
cgcaccaccg gcccatttcg cagcatgcca cagagcggcg tcttgaaagc gggccagacc 720
attcactacg atgaagttat gaaacaggac ggccatgtgt gggtgggcta taccggcaac 780
agcggccagc gtatttattt accggttcgc acctggaata aaagcaccaa taccttaggc 840
gtgttatggg gtaccattaa g 861

<210> SEQ ID NO 14
<211> LENGTH: 801
<212> TYPE: DNA
<213> ORGANISM: Artificial sequence
<220> FEATURE:
<223> OTHER INFORMATION: Staphylococcus simulans and Staphylococcus aureus

<400> SEQUENCE: 14
atggcgagta cattaaatta tttgaaaaca ttagagaata gaggatggga tttcgacggt 60
agttatggat ggcaatgttt cgatttagtt aatgtatatt ggaatcatct ttatggtcat 120
ggattaaaag gatatggagc taaagatata ccatatgcaa ataattttaa tagtgaagct 180
aaaatttatc acaacacacc aactttcaaa gctgaacctg gggacttagt ggtttttagt 240
ggaagatttg gtggaggata tggtcataca gctattgtct taaatggtga ttatgatgga 300
aaattaatga agttccaaag tttagatcaa aactggaata atggtggatg gcgtaaagca 360
gaggttgcac ataaagttgt tcataattat gaaaatgata tgatttttat tagaccattt 420
aaaaaagcaa tgtctaatag caccgcgcag gacccgatgc cgttcttgaa gtcggcgggc 480
tatggcaaag caggcggcac cgtgactccg accccgaaca cgggctggaa aaccaacaag 540
tacggtactc tttacaaaag cgagagcgca tcttttacgc caaacacgga catcatcacg 600
cgcaccaccg gcccatttcg cagcatgcca cagagcggcg tcttgaaagc gggccagacc 660
attcactacg atgaagttat gaaacaggac ggccatgtgt gggtgggcta taccggcaac 720
agcggccagc gtatttattt accggttcgc acctggaata aaagcaccaa taccttaggc 780

-continued

```
gtgttatggg gtaccattaa g                                              801


<210> SEQ ID NO 15
<211> LENGTH: 281
<212> TYPE: PRT
<213> ORGANISM: Artificial sequence
<220> FEATURE:
<223> OTHER INFORMATION: bacteriophage phiK and Staphylococcus simulans

<400> SEQUENCE: 15

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Gly Gly Ser Lys Pro Gly Gly Thr Lys Pro Gly Gly Ser
                165                 170                 175

Lys Pro Gly Ser Thr Val Thr Pro Thr Pro Asn Thr Gly Trp Lys Thr
            180                 185                 190

Asn Lys Tyr Gly Thr Leu Tyr Lys Ser Glu Ser Ala Ser Phe Thr Pro
        195                 200                 205

Asn Thr Asp Ile Ile Thr Arg Thr Thr Gly Pro Phe Arg Ser Met Pro
    210                 215                 220

Gln Ser Gly Val Leu Lys Ala Gly Gln Thr Ile His Tyr Asp Glu Val
225                 230                 235                 240

Met Lys Gln Asp Gly His Val Trp Val Gly Tyr Thr Gly Asn Ser Gly
                245                 250                 255

Gln Arg Ile Tyr Leu Pro Val Arg Thr Trp Asn Lys Ser Thr Asn Thr
            260                 265                 270

Leu Gly Val Leu Trp Gly Thr Ile Lys
        275                 280


<210> SEQ ID NO 16
<211> LENGTH: 843
<212> TYPE: DNA
<213> ORGANISM: Artificial sequence
<220> FEATURE:
<223> OTHER INFORMATION: bacteriophage phiK and Staphylococcus simulans

<400> SEQUENCE: 16

atggcgaaaa cccaggcgga aattaacaaa cgtctggatg cgtatgcgaa aggcaccgtg      60

gatagcccgt atcgtgtgaa aaaagcgacc agctatgatc cgagctttgg cgtgatggaa     120
```

```
gcgggtgcga ttgatgcgga tggctattat cacgcgcagt gccaggatct gattaccgat      180

tatgtgctgt ggctgaccga taacaaagtg cgtacctggg gcaacgcgaa agatcagatc      240

aaacagagct atggcaccgg ctttaaaatc catgaaaaca aaccgagcac cgtgccgaaa      300

aaaggctgga ttgcggtgtt taccagcggc agctatgaac agtggggcca tattggcatt      360

gtgtatgatg gcggcaacac cagcaccttt accattctgg aacagaactg gaacggctat      420

gcgaacaaaa aaccgaccaa acgcgtggat aactattatg gcctgaccca ttttattgaa      480

attccggtgg gcggtagcaa acctggaggc acgaagccgg gtggaagcaa accaggatcg      540

accgtgactc cgaccccgaa cacgggctgg aaaaccaaca agtacggtac tctttacaaa      600

agcgagagcg catcttttac gccaaacacg gacatcatca cgcgcaccac cggcccattt      660

cgcagcatgc cacagagcgg cgtcttgaaa gcgggccaga ccattcacta cgatgaagtt      720

atgaaacagg acggccatgt gtgggtgggc tataccggca acagcggcca gcgtatttat      780

ttaccggttc gcacctggaa taaaagcacc aataccttag gcgtgttatg gggtaccatt      840

aag                                                                    843
```